(12) United States Patent
Deamer et al.

(10) Patent No.: US 10,280,191 B2
(45) Date of Patent: May 7, 2019

(54) NON-ENZYMATIC, SALT-MEDIATED SYNTHESIS OF POLYNUCLEIC ACIDS

(71) Applicants: The Regents of the University of California, Oakland, CA (US); University Pierre and Marie Curie, Paris (FR)

(72) Inventors: David W. Deamer, Santa Cruz, CA (US); Marie-Christine Maurel, Paris (FR); Laura Da Silva, Charvieu (FR)

(73) Assignees: The Regents of the University of California, Oakland, CA (US); Sorbonne Universite, Paris (FR)

( * ) Notice: Subject to any disclaimer, the term of this patent is extended or adjusted under 35 U.S.C. 154(b) by 324 days.

(21) Appl. No.: 15/022,487

(22) PCT Filed: Sep. 16, 2014

(86) PCT No.: PCT/US2014/055951
§ 371 (c)(1),
(2) Date: Mar. 16, 2016

(87) PCT Pub. No.: WO2015/042073
PCT Pub. Date: Mar. 26, 2015

(65) Prior Publication Data
US 2016/0229882 A1 Aug. 11, 2016

Related U.S. Application Data

(60) Provisional application No. 61/879,046, filed on Sep. 17, 2013.

(51) Int. Cl.
| | |
|---|---|
| *C07H 1/00* | (2006.01) |
| *C07H 19/10* | (2006.01) |
| *C07H 19/20* | (2006.01) |
| *C07H 21/02* | (2006.01) |
| *C12N 15/113* | (2010.01) |
| *C12Q 1/6844* | (2018.01) |

(52) U.S. Cl.
CPC .............. *C07H 21/02* (2013.01); *C07H 1/00* (2013.01); *C07H 19/10* (2013.01); *C07H 19/20* (2013.01); *C12N 15/113* (2013.01); *C12Q 1/6844* (2013.01); *C12N 2310/14* (2013.01); *C12N 2330/30* (2013.01)

(58) Field of Classification Search
CPC ........ H04L 51/32; H04L 51/36; H04L 67/104
See application file for complete search history.

(56) References Cited

U.S. PATENT DOCUMENTS

| | | |
|---|---|---|
| 7,772,390 B1 | 8/2010 | Deamer |
| 8,314,209 B2 | 11/2012 | Rajamani et al. |
| 2002/0161219 A1 | 10/2002 | Kanavarioti et al. |
| 2009/0264621 A1 | 10/2009 | Rajamani et al. |

OTHER PUBLICATIONS

Deamer, D., et al., "Bioenergetics and Life's Origins," Cold Spring Harb Perspect Biol (2010) 2:a004929, 17 pp.
Olasagasti, F., et al., "Non-enzymatic transfer of sequence information under plausible prebiotic conditions," Biochimie (2010) 93(3): 556-561.
Rajamani, S., et al., "Lipid-assisted synthesis of RNA-like polymers from mononucleotides," Origins of Life and Evolution of Biospheres (2007) 38(1): 57-74.
Taran, O., et al., "Synthesis of information-carrying polymers of mixed sequences from double stranded short deoxynucleotides," Journal of Systems Chemistry (2010) 1:9, 16 pp.
Toppozini, L., et al., "Adenosine Monophase Forms Ordered Arrays in Multilamellar Lipid Matrices: Insights into Assembly of Nucleic Acid for Primitive Life," Plos One (2013) 8(5): e62810, 6 pp.
Zhang, S., et al., "Synthesis of N3'-P5'-linked Phosphoramidate DNA by Nonenzymatic Template-Directed Primer Extension," J Am Chem Soc (2013) 135:924-932.

*Primary Examiner* — Lawrence E Crane
(74) *Attorney, Agent, or Firm* — Shweta Chandra; Bozicevic, Field & Francis LLP

(57) ABSTRACT

Provided herein is a method for synthesizing polynucleic acids, comprising the steps of (a) providing an acidic solution substantially free of nucleic acid polymerase and lipids, but containing mononucleotides and a monovalent salt; (b) drying and resolubilizing the mixture of step (a) a plurality of times; and (c) recovering polynucleic acids from a resolubilized mixture of step (b). In certain aspects, the method further uses a low pH, e.g. about 3; it can utilize monophosphates, such as AMP rather than ATP; and it can be used with a polynucleotide template to form a sequence at least partially complementary to said template. Thus, both single-stranded and double-stranded polynucleic acids are provided. Ammonia salts have been used to obtain RNA lengths from 10 to 300 nucleotides after 16 half hour cycles and an effective temperature includes between 80° C. and 100° C.

20 Claims, 14 Drawing Sheets
Specification includes a Sequence Listing.

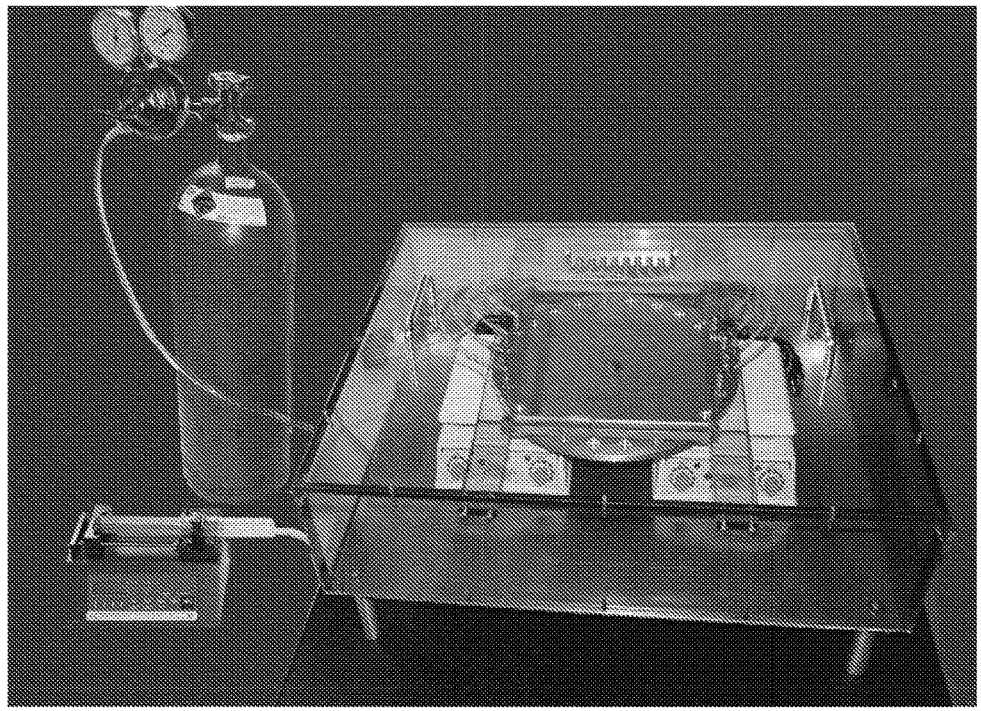
*FIG. 2*
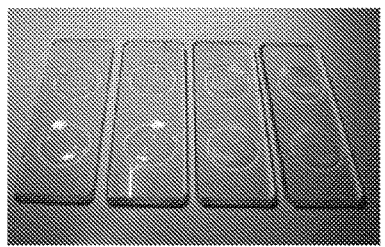  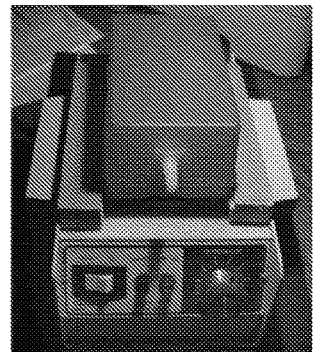
*FIG. 3A*   *FIG. 3B*   *FIG. 3C*

Scan of Longer Polymers in Square Above

```
SEQUENCE LISTING

<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
<223> OTHER INFORMATION: Synthetic

<400> SEQUENCE: 1
acgccaaaaa cauaaagaaa g                                               21

<210> SEQ ID NO 2
<211> LENGTH: 21
<212> TYPE: RNA
<213> ORGANISM: Artificial Sequence
<220> FEATURE:
<223> OTHER INFORMATION: Synthetic

<400> SEQUENCE: 2
uucuuuaugu uuuggcguc u                                                21

<210> SEQ ID NO 3
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: n is abasic site

<400> SEQUENCE: 3
tgcggttttt gtatttcttt cnaagaaata caaaaccgc aga                        43
```

US 10,280,191 B2

NON-ENZYMATIC, SALT-MEDIATED SYNTHESIS OF POLYNUCLEIC ACIDS

CROSS-REFERENCE TO RELATED APPLICATIONS

This application claims priority from U.S. Provisional Patent Application No. 61/879,046, filed on Sep. 17, 2013, which is hereby incorporated by reference in its entirety, and is a national phase filing of PCT Patent Application No. PCT/US2014/055951 filed on Sep. 16, 2014, the disclosure of which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

In accordance with "Legal Framework for EFS-Web," (6 Apr. 11) Applicants submit herewith a sequence listing as an ASCII text file. The text file will serve as both the paper copy required by 37 CFR 1.821(c) and the computer readable form (CRF) required by 37 CFR 1.821(e). The date of creation of the file was Mar. 16, 2016, and the size of the ASCII text file is 1059 bytes. Applicants incorporate the contents of the sequence listing by reference in its entirety.

BACKGROUND OF THE INVENTION

Field of the Invention

The present invention relates to the field of chemical (abiotic) synthesis of polynucleic acids, particularly single stranded and double stranded nucleic acids, such as double stranded RNA.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

It has been reported that RNA-like molecules are synthesized from ordinary mononucleotides if the monomers are organized within a liquid crystalline matrix (Rajamani S, Vlassov A, Benner S, Coombs A, Olasagasti F, Deamer D., "Lipid-assisted synthesis of RNA-like polymers from mononucleotides," Orig Life Evol Biosph. 38:57-74 (2008)). This method is based on providing an aqueous suspension of phospholipid vesicles and monomers, and subjecting the mixture to alternating cycles of hydration and dehydration, hereafter referred to as HD cycles.

It has also been demonstrated that under the same conditions sequence information could be transferred non-enzymatically from a template strand of DNA to product strands (Olasagasti F, Kim H J, Pourmand N, Deamer D W. 2011, "Non-enzymatic transfer of sequence information under plausible prebiotic conditions," Biochimie. 93:556-61). In this report, an environment was created where dry and wet periods were cycled. Under anhydrous conditions, lipid molecules present in the medium could form fluid lamellar matrices and work as organizing agents for the condensation of nucleic acid monomers into polymers on a DNA template strand.

Toppozini L, Dies H, Deamer D W, Rheinstädter MC (2013) Adenosine Monophosphate Forms Ordered Arrays in Multilamellar Lipid Matrices: Insights into Assembly of Nucleic Acid for Primitive Life. PLoS ONE 8: e62810 discloses the use of X-ray diffraction analysis to show that adenosine monophosphate forms a two-dimensional ordered array when it undergoes the dehydration step of an HD cycle within a multilamellar matrix of dimyristoyl-phosphatidyl-choline.

Deamer U.S. Pat. No. 7,772,390, entitled "Lipid mediated nucleic acid synthesis," issued Aug. 10, 2013, discloses methods in which lipids and monomeric precursors, e.g., mononucleotides, of the desired polymeric products are combined to produce a reaction mixture. The reaction mixture is then subjected to one or more steps of drying and rehydrating to produce a desired polymeric product, e.g., nucleic acid.

Rajamani et al. U.S. Pat. No. 8,314,209, entitled "Lipid-assisted synthesis of polymer compounds and methods for their use," issued Nov. 20, 2012, discloses a method that provides for the synthesis of polynucleotides from mononucleotides in the absence of catalytic enzymes. The method comprises providing an aqueous solution having a plurality of phospholipid molecules and monomer molecules; subjecting the aqueous suspension to fluctuating cycles of drying and hydrating conditions at elevated temperature ranges; subjecting the aqueous solution to fluctuating [H+] conditions; the fluctuating conditions thereby allowing formation of a chemical bond between at least two monomers to create a polymer.

BRIEF SUMMARY OF THE INVENTION

The following brief summary is not intended to include all features and aspects of the present invention, nor does it imply that the invention must include all features and aspects discussed in this summary.

The present invention pertains to a method for in vitro method for synthesizing polynucleic acids ("polynucleotides") from mononucleotide precursors using monovalent salts as organizing agents and other conditions. According to the present invention, double stranded and single stranded RNA may be produced. The RNA produced by the present methods has been shown to be polymeric and of a native structure sufficient to be digestible by RNase A. In addition, the present methods may be used for replication of a polymeric nucleotide template, using a non-enzymatic polymer chain reaction.

The present invention comprises an in vitro method for synthesis and recovery of polynucleotides, wherein said polynucleotides have a directed sequence, based on a template polynucleotide added to the reaction solution. In addition, the invention contemplates the creation of libraries of polynucleotides, such as RNA polymers, wherein the library contains a diverse population of different sequences. Such libraries are useful, for example, in the identification of RNA or DNA aptamers, and the study of RNA diversity in evolution.

Thus, the present invention may comprise, in certain aspects, a method for synthesizing polynucleic acids, comprising: providing an acidic solution substantially free of polymerase and lipids, but containing mononucleotides and a dissolved monovalent salt in high concentration; drying and resolubilizing the solution a plurality of times; and recovering polynucleic acids from a resolubilized mixture.

The present invention may comprise, in certain aspects, a method for synthesizing RNA polynucleic acids, comprising the steps of: (a) providing an acidic solution containing 5'-mononucleotides such as adenosine monophosphate (A), uridine monophosphate (U), guanosine monophosphate (G) and cytidine monophosphate (C) in acidic form, together with a monovalent salt, such as a metal-halogen salt in high concentration; (b) drying and resolubilizing the solution of step (a) a plurality of times; and (c) recovering polynucleic acids from a resolubilized mixture of step (b). The nucleotides used do not require chemical activation and may contain a native or natural structure at the 5' monophosphate terminus.

The present invention may comprise, in certain aspects, a method as referred to above wherein the acidic solution is adjusted to a pH between 2 and 4 during the synthesis of the polynucleic acid according to the present process. The present invention may comprise, in certain aspects, a method as referred to above wherein the mononucleotides added to the mixture are monophosphates. The present invention may comprise, in certain aspects, a method as referred to above wherein the mononucleotides comprise A, U, G, and C in various combinations. The mononucleotides added to the solution may be added in a ratio of equal amounts of each of the four bases, or certain bases may be omitted or increased, depending on the goals of the synthesis. In cases of DNA synthesis, deoxyribonucleotides and thymidylic acid (T) may also be used in place of U. The present invention may comprise, in certain aspects, a method as referred to above comprising the step of adding a polynucleotide template to the solution and said wherein recovering comprises recovering polynucleic acids produced in the process having a sequence at least partially complementary to said template.

The salt or salts used in the present method may be present in a range of concentrations, up to saturation. In certain embodiments, the monovalent salt(s) are present in a concentration in solution of from 0.05 and 2M or from 0.001 to 3M or from 0.05 to 1 M (See "Ranges" for further variations).

The present invention may also comprise, in certain aspects, a method as referred to above wherein the step of recovering polynucleic acids thereby produced comprises recovering double stranded polynucleic acids, that is, partially or fully double-stranded, e.g. as shown in FIG. 12. The present invention may comprise, in certain aspects, a method as referred to above wherein the double stranded polynucleic acids are predesigned according to a certain sequence and be a short interfering RNA.

The above-mentioned recovering may comprise recovering polynucleotides having a sequence length greater than 20 bases, greater than 100 bases, or greater than 200 bases.

The present invention may also comprise, in certain aspects, a method as referred to above wherein the monovalent salt is selected from the group consisting of NaF, CsCl, NaBr, NaClO$_4$, NaCl, KCl, and NH$_4$Cl. The present invention may comprise, in certain aspects, a method as referred to above wherein the salt is an ammonium salt (e.g. NH$_4$-halo), a tetramethylammonium salt or another halide salt (including and additional to the halide salts listed above).

The present invention may also comprise, in certain aspects, a method as referred to above further comprising the step of heating the solution, e.g. to a temperature between 80° C. and 100° C.

The above methods are abiotic, that is, without use of biological mechanisms such as cells or polymerase. The above methods are preferably carried out under anaerobic conditions. The present methods are also independent of the use of organizing macromolecules such as lipids or similar lamellar matrices. In certain embodiments, the present invention comprises the use of an automatable device that holds the reactants for a defined period, controlling heating (drying) and resolubilization with salt solutions, and further controlling the atmosphere in the device to be low in oxygen, e.g. creating a $CO_2$ atmosphere.

In certain embodiments, the present invention comprises an in vitro method for synthesizing polynucleic acids from a plurality of mononucleotides, comprising the use of an acidic solution substantially free of polymerase and lipids, but containing mononucleotides and a monovalent salt at a concentration of at least 0.01 M; drying the solution; resolubilizing the solution; and repeating drying and resolubilizing steps a plurality of times. Afterwards, the result will be the formation of bonds between the mononucleotide. Then, the method comprises recovering (i.e. separating) polynucleic acids from a resolubilized mixture.

In certain embodiments, the present invention comprises heating the solution during drying. In certain embodiments, the present invention comprises the use of an acidic solution adjusted to a pH between 2 and 4, or between 2 and 6. In certain embodiments, the present invention comprises the addition to the solution of mononucleotides are monophosphates (as opposed e.g. to salts) and the mononucleotides are present at a concentration of at least 1 millimolar. In certain embodiments, the present invention comprises the use of mononucleotides comprising dAMP, dTTP, dGMP, and dCTP or AMP, UMP, GMP, and CMP, using the standard abbreviations for DNA and RNA bases, respectively.

In certain embodiments, the present invention comprises the use of a polynucleotide template. The present methods then will also comprise recovering polynucleic acids having a sequence at least partially complementary to said template. The step of recovering polynucleic acids may comprise recovering double stranded polynucleic acids, which may be partially or completely double stranded.

In certain embodiments, the present invention comprises the in vitro synthesis of double stranded polynucleic acids are short interfering RNAs.

In certain embodiments, the present invention comprises the use of a monovalent salt is one or more selected from the group consisting of NaF, CsCl, NaBr, NaClO$_4$, NaCl, KCl, and NH$_4$Cl and said salt concentration is between 0.05 M and 2M in solution. In certain embodiments, the salt is a tetramethylammonium salt. In certain embodiments the salt is a halide (halogen salt).

In certain embodiments, the present invention comprises the step of heating the solution. In certain embodiments the heating is to a temperature between 80° C. and 90° C.

In certain embodiments, the present invention comprises methods as described above wherein the recovering comprises recovering polynucleotides having a sequence length greater than 200 bases.

In certain embodiments, the present invention comprises methods as described above wherein the reaction is carried out under anaerobic conditions.

In certain embodiments, the present invention comprises methods as described above wherein the monovalent salt concentration is between 0.05 and 2M in solution.

In certain embodiments, the above-described methods result in inventive systems. That is, the invention may comprise or consist essentially of a system for use in preparing a polynucleotide of a desired sequence, comprising: an solution adjusted to be between pH 2 and 4, free of polymerase and lipids; said solution comprising a mononucleotides A, U, G, and C, each at a concentration of from 0.001 to 3M; a monovalent salt selected from the group consisting of NaF, CsCl, NaBr, NaClO$_4$, NaCl, KCl, and NH$_4$Cl; and a template polynucleotide complementary to the desired sequence; said solution further maintained in the system at an anerobic environment. The invention in certain aspects comprises a system for use in preparing polynucleotides, comprising or consisting essentially of: a dried solution, free of polymerase and lipids; said dried solution comprising a mononucleotides A, U, G, and C, each at a concentration of from 0.001 to 3M if the liquid; a monovalent salt selected from the group consisting of NaF, CsCl, NaBr, NaClO$_4$, NaCl, KCl, and NH$_4$Cl; and a template polynucleotide complementary to the desired sequence; said dried solution further maintained in the system at an anerobic environment.

BRIEF DESCRIPTION OF THE DRAWINGS

FIG. 1A is a schematic diagram showing formation of phosphodiester bonds between monomers in acid form (rather than salt form) in the presence of a monovalent salt as used in the present methods. As can be seen, an H+ will react with the P=O, then a water leaves when the phosphodiester bond is formed. FIG. 1B illustrates hydrogen bonding between a mononucleotide illustrated in FIG. 1A and a uridine monophosphate; FIG. 1C shows the arrangement of nucleotides within a semi-crystalline matrix established by the salt concentration in the present methods. The schematic indicates the edge of a salt crystal. The reaction takes place in the concentrated salt solution between the crystals. Bases 1, 2 and 3 may be added in oligomeric form as template upon which a second strand is formed in a complementary sequence.

FIG. 2 is a photograph of a chamber that cycles potential reactants between hydrated and dehydrated states. There are 24 wells in the central disk that hold reactants, and a stepper motor rotates the disk 15 degrees every 30 minutes. The rotation brings the samples over two heat sources, and dry carbon dioxide flows into four sample wells on each side of the disk to aid dehydration. The chamber is filled with carbon dioxide to exclude oxygen, and water is delivered to samples by a programmable syringe pump.

FIG. 3A, 3B, 3C is a series of photographs of a small HD (heat and dry) apparatus in which cycling is carried out by hand. The samples are contained in two wells in each slide, so that 8 samples can be processed in parallel. To aid drying, carbon dioxide gas is delivered into the wells through the flow box shown on the right.

FIG. 13A is a phase image; FIG. 13B is a fluorescent image, excited by 360 nM UV illumination. 160X original magnification.

DETAILED DESCRIPTION OF THE PREFERRED EMBODIMENT

Overview

The present invention pertains to the non-enzymatic synthesis of polynucleic acids from short precursor molecules, preferably native nucleic acid monomers. The present methods are carried out in vitro, i.e. without the use of cells or other organisms; they are carried out under synthetic conditions. They are applicable to forming single-stranded and double-stranded RNA and DNA from pre-defined mixtures of mononucleotides under defined conditions described below. An important feature of the present method is the ability of the method to produce multiple copies of polynucleotides of defined sequence based on a template sequence. That is, multiple copies of a polynucleotide (DNA or RNA) having a predefined sequence may be made. The template strands (which may be the same or different sequences) are added along with the necessary monomers (AMP, UMP, GMP, CMP in the case of RNA, or, in the case of DNA, dAMP, dTMP, dGMP, dCMP). Also added are monovalent salts and a pH lowering agent (acid). The monomers are added in their free acid monophosphate form, e.g. adenosine monophosphate, uracil monophosphate, guanine monophosphate, thymine monophosphate, etc. No enzymes or lipids are used for the polymerization. Accordingly, non-natural bases may also be incorporated into the template and/or the resulting copies.

Figure 1A:
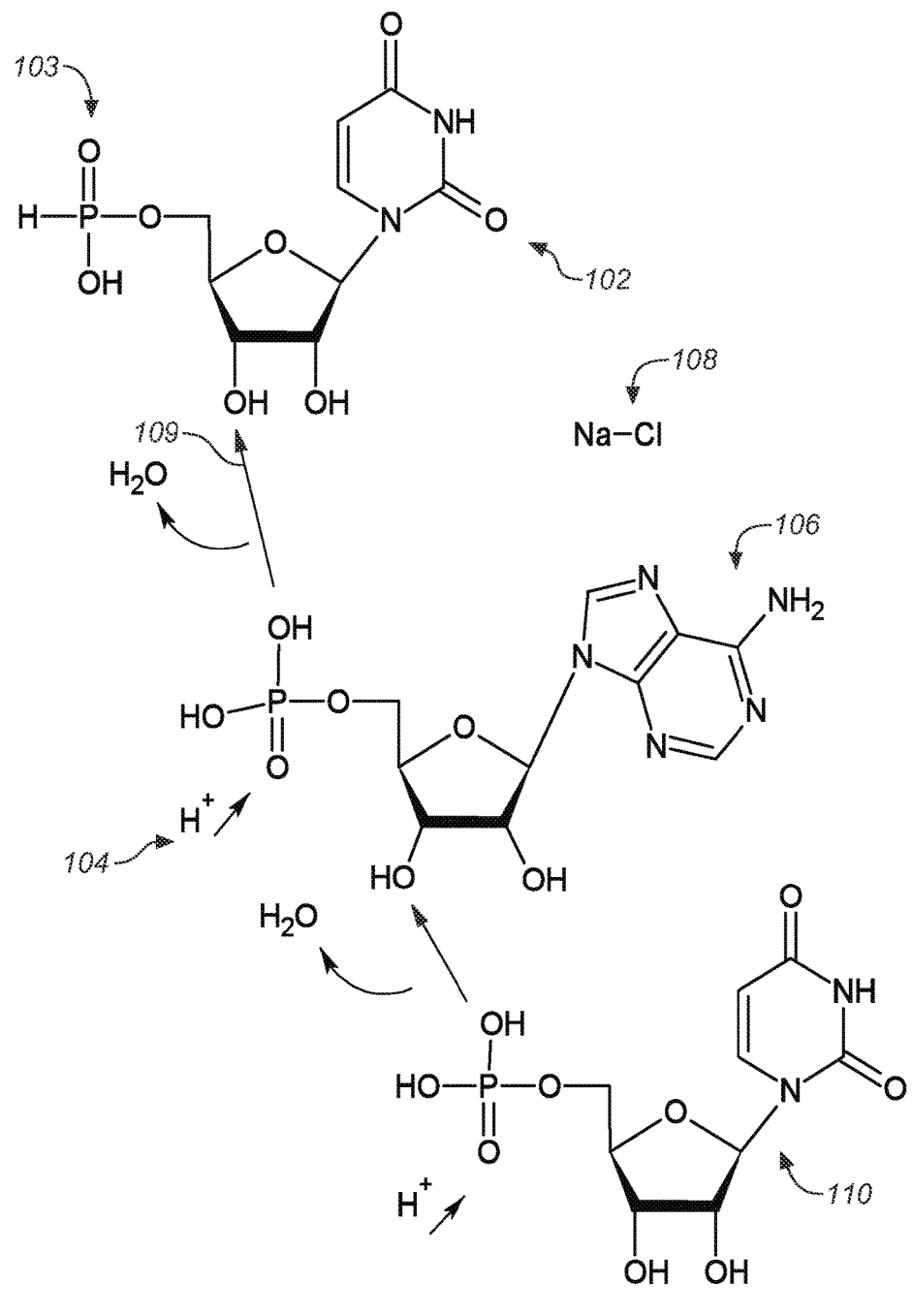
FIG. 1A, 1B, 1C.

A representative reaction of 5' uridine monophosphate 102 with a 5' phosphate group 103, i.e. in acidic form, as also shown at 104 and 5' adenosine monophosphate 106 is shown in FIG. 1A. The reaction occurs in an aqueous environment with a monovalent salt, illustrated as NaCl at 108, but which could also be ammonium chloride, etc. Nucleotides 102 and 106 combine to form a phosphodiester bond as indicated by arrow 109, forming a 3'-5' linkage. A third 5' monophosphate base 110 can also form a 3'-5' linkage with the base 106, and so forth with other monomers. This forms a single stranded polynucleotide. In certain instances, a 2'-5' linkage may be formed. Evidence for this polynucleotide structure is provided by RNase A experiments. RNase A cleaves specifically after pyrimidine nucleotides. Cleavage takes place in two steps: first, the 3', 5'-phosphodiester bond is cleaved to generate a 2', 3'-cyclic phosphodiester intermediate; second, the cyclic phosphodiester is hydrolyzed to a 3'-monophosphate.

Figure 1B:
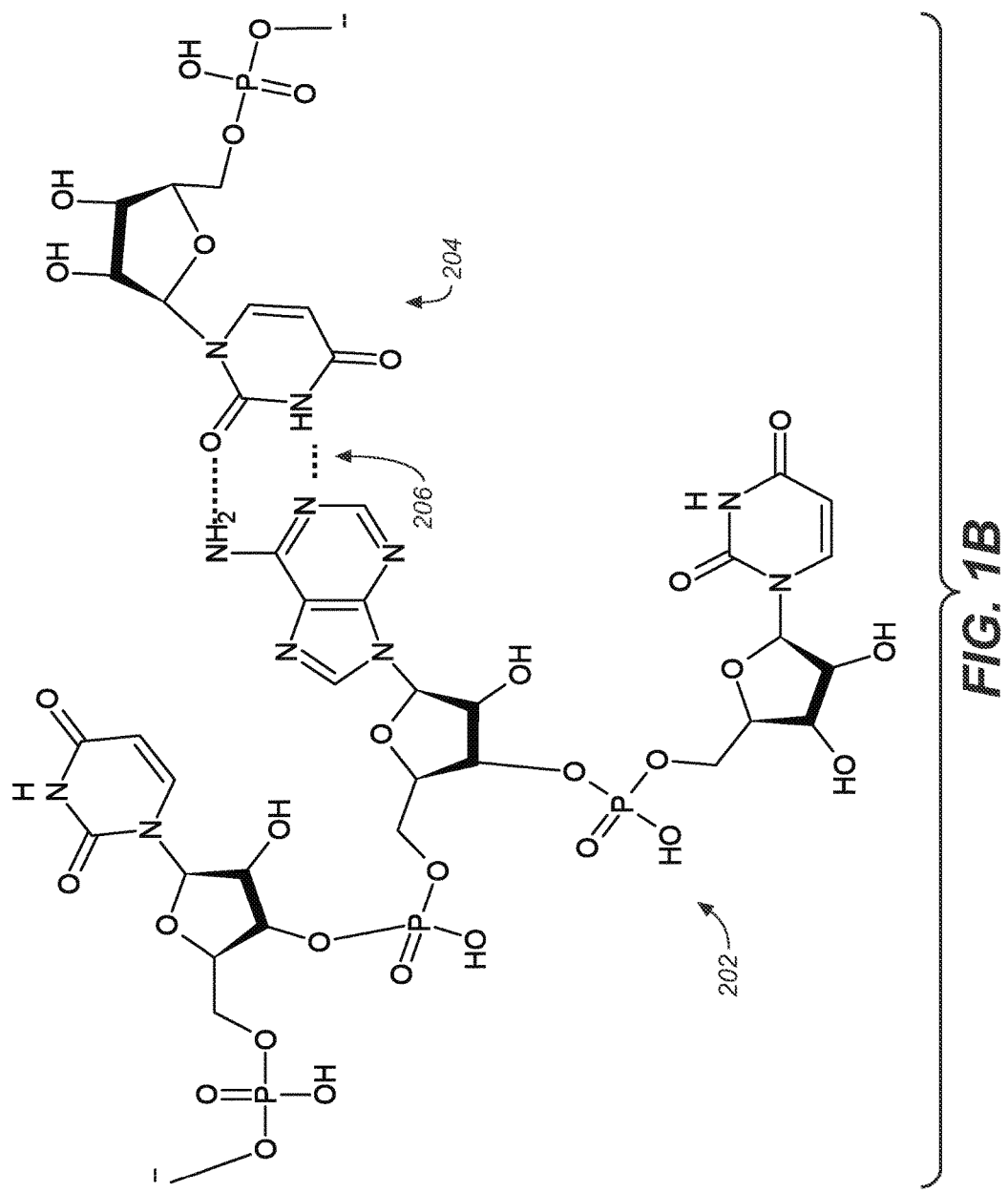

As shown in FIG. 1B, the polymerization scheme shown in FIG. 1A can be used to form a template molecule 202 to which complementary bases 204 can be formed, with base pairing as shown by dotted lines 206. As described below, preformed templates can be added to direct synthesis to form a desired sequence.

Figure 1C:
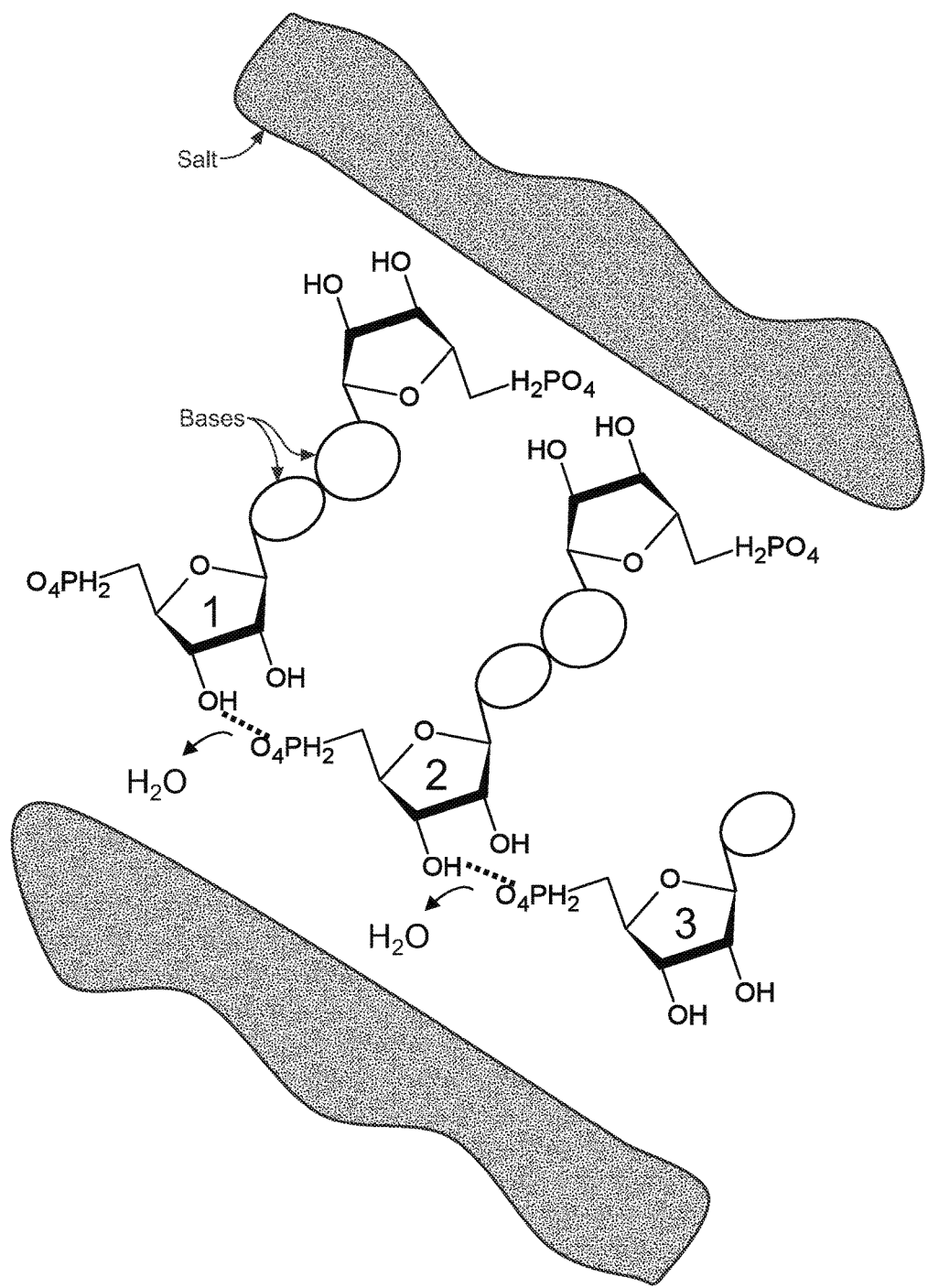

As shown in FIG. 1C, the salt concentration in the mixture of the present method is thought to drive the monophosphate nucleotides into close proximity, and also into an orientation where base pairing and base stacking can occur. In this orientation, the phosphate groups are in close proximity to the —OH groups of a neighboring ribose, an arrangement conducive to synthesis of phosphodiester bonds that link the AMP and UMP monomers into a nucleic acid polymer. Also shown is the formation of dsRNA; in certain embodiments, described below, bases 1, 2 and 3 will be added by pairing with a template strand rather than as individual monomers. This is indicated by a dashed line between phosphate and hydroxyl groups in bases 1, 2 and 3. A phosphate linkage will also form between the third carbon of one ribose and the fifth carbon of the next ribose in pairing with the template.

The present methods can be used to produce oligonucleotides of 300 nt or more. The present methods are characterized in that they do not employ enzymes such as are conventionally used in synthesizing oligonucleotides, and they do not employ lipids to concentrate the nucleotides. To reiterate, no enzymes (e.g. polymerase) or other biological structures are added to the reaction mixture. Thus, the reaction solution may be free of enzyme co-factors. The term co-factors here is meant to refer to $Mg^{2+}$, $Mn^{2+}$, $Ca^{2+}$, $ATP$, $NAD^+$, $NADP^+$, diacylglycerol, phosphatidylserine, eicosinoids, retinoic acid, calciferol, ascorbic acid, neuropeptides, enkephalins, endorphins, 4-aminobutyrate (GABA), 5-hydroxytryptamine (5-HT), catecholamines, acetyl CoA, S-adenosylmethionine, hexose sugars, pentose sugars, phospholipids, lipids, glycosyl phosphatidyl inositols (GPIs), and any other biological cofactor.

The pH of the reaction mixture should be between about 1 and 6, preferably between 2 and 3-4 during the multiple HD cycles that will be run. The reaction should be run under anaerobic conditions. Anaerobic conditions may include substantial absence of oxygen including free oxygen or bound oxygen ($NO_2$, $NO_3$), and may include, for convenience, the sequestration of a reaction from atmospheric air. By way of illustration, anaerobic conditions can be those with less than 1 mg dissolved oxygen per liter of reaction mixture.

Figure 12:
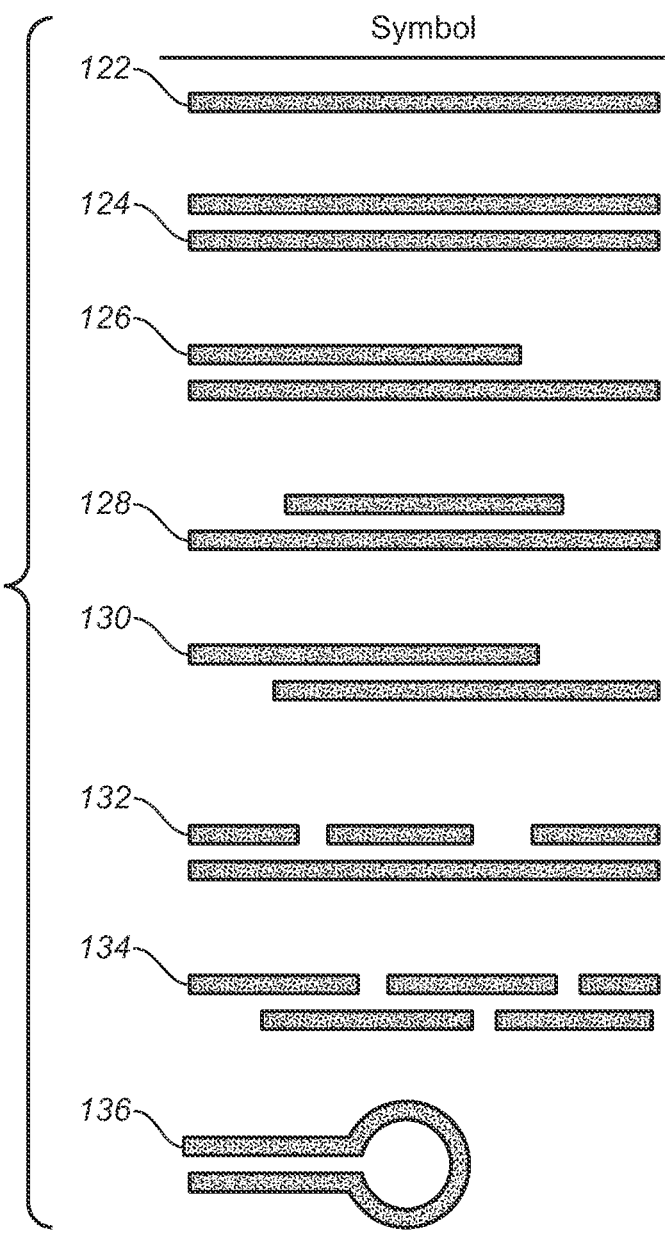
FIG. 12 is a diagram showing possible dsRNA products synthesized by HD cycles. The lengths and sequences shown are arbitrary, and are for illustration purposes only.
Figure 13A:
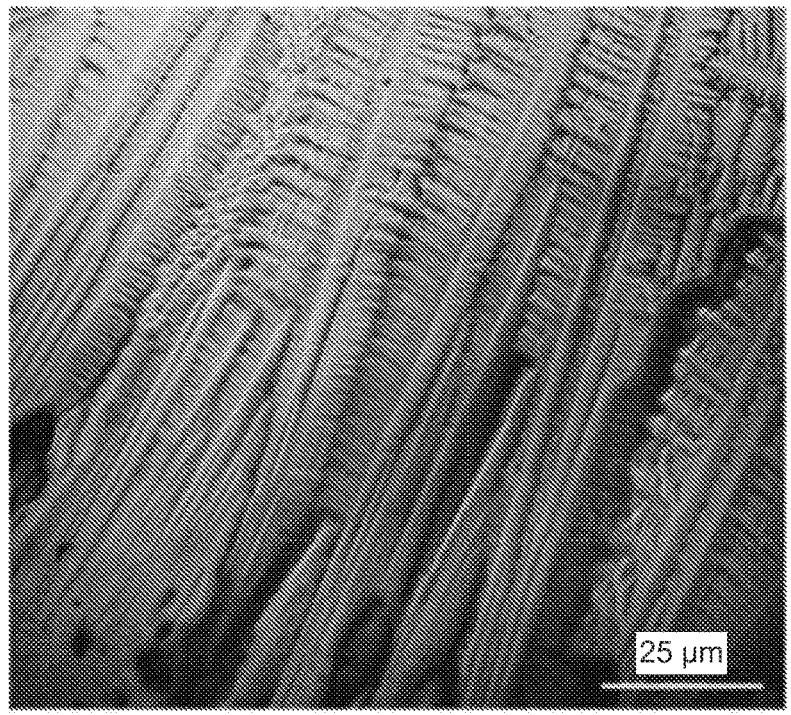
FIG. 13A, 13B is a pair of micrographs showing salt crystals formed under conditions of the present process, showing the possibility that the salts in the process organize the nucleotides. These experiments used 50 µl 0.1M NH$_4$Cl+5 mM AMP+5mMUMP+0.1 mM pyramine, dried one hour at 85 deg. C.
Figure 13B:
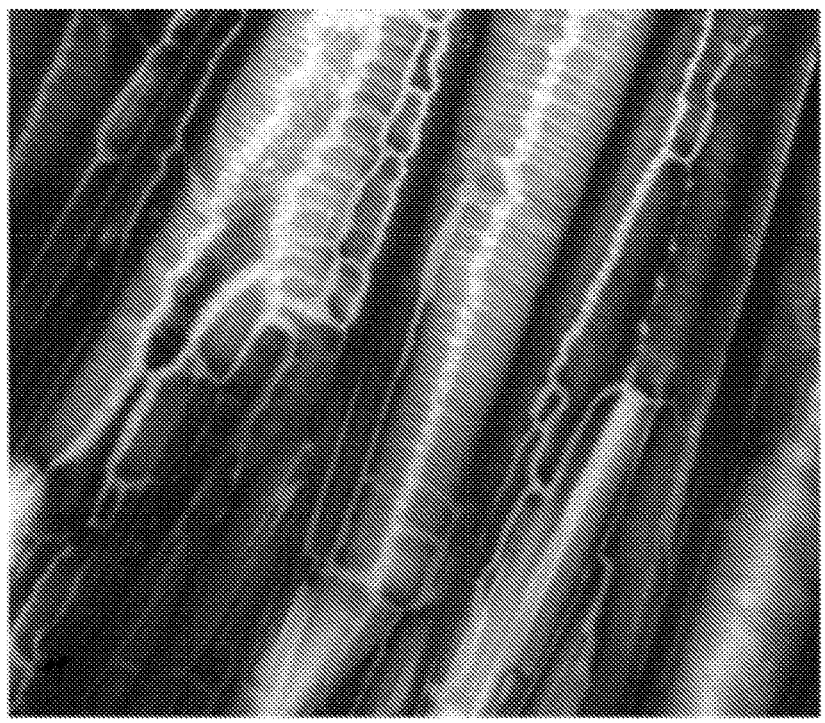

The present methods may be used to form double stranded polymers, such as dsRNA, as shown e.g. in FIG. 12. Generally, a polynucleotide will be used as a template when a predetermined sequence is desired. Other examples of double stranded RNA may be found, e.g. in WO 2007031322 A1, "Compositions comprising immunostimulatory RNA oligonucleotides and methods for producing said RNA oligonucleotides." Referring now to FIG. 12, the possible random single-stranded and double-stranded RNA oligomers are a linear sequence, 122; a double-stranded oligomer, 124; a partially double-stranded oligomer 126; a partially double stranded oligomer with a partially central double-stranded portion 128; a partially double stranded oligomer with a 5' overhang (could also be 3' overhang) 130; intermediate partial double-stranded structure 132; multiply fragmented double-stranded structure 134; and a hairpin structure 136.

The polymerization reaction described here can be carried out with about 1-20, 1-15 or 1-10, and usually about 1-7 or 4-7 cycles of wetting and drying. The cycle starts with admixing of the salt solution and nucleic acid materials (monomers and template(s)) and any other excipients to produce the fluid reaction mixture. The pH of the fluid reaction mixture can vary, but is usually in a pH range of around 2 to 4. This includes a pH of the reaction mixture with fractional increments of 0.1, 0.2, 0.3, 0.4, 0.5, 0.6, 0.7, 0.8, 0.9 and 1.0 over a pH range of about 2, 3, 4, 5, and 6. The mixture may be buffered or un-buffered and include one or more additional excipients such as a detergent and the like.

Drying also may include subjecting the reaction mixture to a non-streaming gas or vacuum (e.g., lyophilization). In another embodiment, drying is accomplished by a combination of a stream of gas and lyophilization. Drying refers to the lack of liquid such that the dried material presents a solid appearance. Drying may also be carried out under variable temperature and/or pH. For instance, the fluid reaction mixture can be dried at a temperature that minimizes inhibition of polymerization or degradation of the reactants and polymerization product, while maximizing the drying process. Temperature ranges for drying include below 0 degree C. to around 100° C. Temperature ranges of specific interest for drying generally include increments of 1, 2, 3, 4, 5, 6, 7, 8, 9 and 10 degrees over a range of about 0, 10, 20, 30, 40, 50, 60, 70, 80, 90 and 100° C.

While the dried reaction mixture can be immediately rehydrated, the dried reaction mixture may also be allowed to incubate for a period of time sufficient for polymerization of monomer. Reaction times are generally chosen so as to optimize polymerization. Exemplary incubation times for the dried reaction mixture are 5 minutes or longer and typically include increments of 0.1, 0.2, 0.3, 0.4, 0.5, 0.6, 0.7, 0.8, 0.9, 1, 2, 3, 4, 5, 6, 7, 8, 9 and 10 minutes of a range of about 10, 20, 30, 40, 50, 60, 70, 80, 90, 100, 110, 120, 130, 140, 150, 160, 170 or 180 minutes or longer (e.g., overnight, or even longer such as when placed in short or long term storage), and more typically 30 minutes to 120 minutes. The dried reaction mixture can be sampled and tested, stored for later use, or followed by a rehydration step during which the lipid matrix is re-solvated.

Rehydration of the dried reaction mixture generates a nucleic acid product that has been synthesized via a condensation reaction from the mononucleotides present in the mononucleotide composition. Rehydration generally takes between 5 and 30 minutes depending on reaction volume, gas exposure and heating. For example, rehydration takes on average about 1 minute for a 0.5 ml reaction volume under a stream of carbon dioxide at around 90° C. The rehydration solvent can be the same solvent system employed in the first cycle, and is usually a weak aqueous protic acid solution with or without buffer.

Anaerobic Heating and Drying Cycles

A chamber was constructed to carry out HD cycles under anaerobic conditions (FIG. 2). Glass vials (1.5 mL) containing reaction mixtures to be tested are placed in 24 wells in an aluminum disk, and the chamber is filled with an inert gas such as carbon dioxide. The disk is heated to a desired temperature, and rotation of the disk is controlled by a programmed stepper motor. As the disk rotates in steps of 15 degrees every 30 minutes, the samples are dehydrated by a flow of dry carbon dioxide through four ports on either side of the disk. Each vial is dried for 2 hours as it rotates under the gas flow, then the rotation brings the vial under a port through which water flows at a rate of 0.4 mL in 15 minutes. The water is injected at a constant rate by a programmable syringe pump. The result is that in a 24 hour period every sample undergoes four cycles of wetting and drying. The $CO_2$ maintains anaerobic conditions and carries away water molecules produced during ester bond synthesis, thereby preventing back reactions of hydrolysis.

Smaller scale experiments were also carried out using glass slides with two wells on each slide that hold 0.1 mL of the reaction mixture. Four slides could be arranged on a laboratory hot plate set at the desired temperature range, and a plastic flow box with 8 small holes (1 mm diameter) was set on the slides. Each hole was placed directly over a well so that carbon dioxide gas flowed onto the mixture. A flow meter monitored the gas flow which was set at 2 cc/sec into each well. The purpose of the gas was to exclude oxygen and to carry away water vapor as it left the reaction mixture. Each HD cycle was 30 minutes, rather than the 2 hour cycle in the larger chamber.

The examples below confirm that drying—rehydration cycles at moderately elevated temperature ranges provide sufficient chemical potential to drive the synthesis of phosphodiester bonds between nucleoside monophosphates.

A polymer that has physical and chemical properties of RNA is synthesized by HD cycles, and monovalent salts unexpectedly improve yields by ten-fold or more. Furthermore, it is shown here that RNase A acts on the presently prepared products of AMP and UMP, with 90% disappearing from gels after an one hour incubation. This result confirmed that UMP had been incorporated into the polymer, because RNase A attacks pyrimidine bonds.

Remarkably, when both AMP and UMP are present, the products appear to have significant duplex character as indicated by multiple analytical methods. This represents the first time that a double stranded nucleic acid has been synthesized in the absence of enzymes or activated substrates. The implication is that such reactions can give rise to double stranded polymers by what is essentially self-assembly.

In summary, double stranded nucleic acids having random sequences of nucleotide bases are synthesized by multiple hydration-dehydration cycles when monovalent salts are present in the mixture. The monovalent salts include NaCl, KCl, and $NH_4Cl$. LiCl does not promote polymerization. The polymers result from a reaction mechanism involving an acid-catalyzed ester bond synthesis with a pH optimum near 3. Feeding additional mononucleotides markedly increases yields, supporting the claim that amplification occurs.

The preparation of libraries of random RNA sequences has a number of uses. For example, Stich et al., "On the structural repertoire of pools of short, random RNA sequences," J. Theoretical Biol. 252(4): 750-763 (2008) investigated computationally the structural properties of a large pool ($10^8$ molecules) of single-stranded, 35 nt-long, random RNA sequences. They reported that the distribution of RNA structural motifs within pools of random sequences is extremely heterogeneous, as theoretical studies and observation of natural secondary structures demonstrate. A main concern of experimentalists seeking new ribozyme or aptamer activities is how to deviate the structural composition of the initial pools in the in vitro experiments from average expectations, thus enhancing for instance the presence of rare structures, or forcing the ensemble to be structurally biased towards specific common structures. A library of RNA molecules of length 35 nt consisting of random linear sequences composed of the four types of nucleotides A, C, G, and U as studies may be prepared in an actual pool, instead of merely computed as reported by these authors. The pool may then be tested against various targets, or otherwise analyzed. It is known that the length of ligand binding aptamer motifs can be easily reduced to 25-30 nt and in some cases to even smaller molecules with as few as 12-13 nt. These lengths are readily achievable using the present methods.

FIG. 12 illustrates the kinds of single stranded and duplex (fully and partially double-stranded) products that might be present in the mixture. These can be identified by using nanopore analysis, mass spectra, sequencing, etc. Nanopore analysis will indicate the length and strandedness of the product. See, e.g. US 20120094278 for details on nanopore polynucleotide analysis.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The abbreviation "HD" refers to heating and drying cycles, where the present liquid solutions are heated and dried while containing the reactants used to form the nucleic acid polymers. The sample is heated and dried, then reconstituted, in a period of time that is desirably about 0.1 to 6 hours, but may be between 0.1 hours and 20 hours. Drying may be carried out by introducing a drying gas to the solution. Heating may be to any temperature above room temperature, up to about 100 degrees C., but preferably not above 90 degrees C. The present process typically employs multiple HD steps in a single synthesis.

Ranges: For conciseness, any range set forth is intended to include any sub-range within the stated range, unless otherwise stated. As a non-limiting example, a range of 120 to 250 is intended to include a range of 120-121, 120-130, 200-225, 121-250 etc. The term "about" has its ordinary meaning of approximately and may be determined in context by experimental variability. In case of doubt, "about" means plus or minus 5% of a stated numerical value.

The term "solution" as used herein refers to ordinarily solid material contained in a liquid carrier. The term is not, unless otherwise noted, limited to true solutions, and may also refer to suspensions or other liquid mixtures.

The term "mononucleotide" as used herein refers to a single nucleotide that can be covalently linked to one or more other such entities to form a polymer. In certain embodiments, the mononucleotides have first and second sites (e.g., 5' and 3' sites) suitable for binding to other like monomers by means of standard chemical reactions (e.g., nucleophilic substitution), and a diverse element which distinguishes a particular monomer from a different monomer of the same type (e.g., a nucleotide base, etc.). In the art synthesis of nucleic acids of this type utilizes an initial substrate-bound monomer that is generally used as a building-block in a multi-step synthesis procedure to form a complete nucleic acid. Exemplary mononucleotides are 5' adenosine monophosphate (AMP) and 5' uridine monophosphate (UMP) as monomers, which can be purchased from Sigma-Aldrich as free acids.

The term "nucleoside" is used in its conventional sense to refer to glycosylamines that can be thought of as nucleotides without a phosphate group. A nucleotide is composed of a nucleobase (also termed a nitrogenous base), a five-carbon sugar (either ribose or deoxyribose), and one or more phosphate groups while a nucleoside consists simply of a nucleobase and a 5-carbon sugar. In a nucleoside, the base is bound to either ribose or deoxyribose via a beta-glycosidic linkage. Examples of nucleosides include cytidine, uridine, adenosine, guanosine, thymidine and inosine.

The term "nucleotide" is used in its conventional sense as a compound composed of a phosphate group, the bases adenine, cytosine, guanine, and thymine, and a pentose sugar, in RNA the thymine base being replaced by uracil. The term also includes heterocyclic bases that have been modified. Such modifications include methylated purines or pyrimidines, acylated purines or pyrimidines, alkylated riboses or other heterocycles.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. The term nucleotide, as is commonly understood, refers to monophosphate, diphosphate, or triphosphate nucleosides.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2-50 monomers, such as about 2-20, and including about 3-10 monomers.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides. Unless specified otherwise, the term refers to naturally occurring RNA, as well as modified RNA such as RNAs containing non-natural nucleosides or sugars. A listing of RNA modifications may be found, e.g. in "The RNA Modification Database," http (colon slash slash) mods.rna.albany.edu/home.

The term "oligonucleotide" as used herein denotes single-stranded nucleotide multimers of from about 10 up to about 200 nucleotides in length, e.g., from about 25 to about 300 nucleotides ("nt"), including from about 50 to about 175 nt, e.g. 150 nt in length.

The term "polynucleotide" or "polynucleic acid" is used in the conventional sense and refers to single- or double-stranded polymers composed of nucleotide monomers, including oligonucleotides, wherein nucleotide monomers are covalently bonded in a chain. DNA (deoxyribonucleic acid) and RNA (ribonucleic acid) are examples of polynucleotides with distinct biological function. Although DNA and RNA do not generally occur in the same polynucleotide, the four species of nucleotides may occur in any order in the chain.

The term "salt" is used in the conventional sense and refers to materials in solid form or in solution formed from an anion(s) and a cation(s). The term monovalent refers to an atom, ion, or chemical group with a valence of one, which thus can form one covalent bond. The present monovalent salts may include for example, alkali metal salts (e.g. alakali metal halides) double salts, and may include metal salts, such as NaF, CsCl, NaBr, $NaClO_4$, imidazole hydrochloride, etc., as well as those listed below.

As used herein a "high salt concentration" can be any concentration of salt that is effective to increase polymerization in the absence of an organizing macromolecule such as a lipid. Preferably, the aqueous high salt concentration solution can be any concentration from 50 mM to 3M, preferably from about 0.1 M to about 2M. The salt that can be used in this invention can be sodium chloride, potassium chloride, calcium chloride, and the like. This dilute peracetic acid sterilizing solution with high salt concentration does not need to be pH adjusted.

The term "acidic" is used in the conventional sense, i.e. a pH below 7. As exemplified below, and acidic pH range can cover a variety of ranges, e.g. 1-5, 1-6, 2-6, 3-5, 2-5, etc. (see reference to "Ranges" above).

As used herein, the phrase "anerobic" means reaction conditions wherein the reaction mixture is not exposed to air or oxygen. In various contexts, a reaction in anaerobic conditions may refer to a reaction environment completely free of oxygen, essentially free of air, free from introduction of air, replacement of air by a non-reactive gas, etc.

The term "short interfering RNA" or siRNA is used in the conventional sense double-stranded RNA that resemble the products produced by DICER and specifically inhibit gene expression in many different mammalian cell lines. Small interfering RNA (siRNA) is typically an oligonucleotide of about 21 nucleotides (also 21 bases) in length which is used in RNA interference. The process begins with dsRNA (double stranded RNA) which is broken down with the help of Dicer into small fragments approximately 21 nt in length. These siRNA fragments have 2 nucleotide overhangs on their 3' ends. Argonaute2 then helps to incorporate siRNA into RISC (RNA-induced silencing complex). This RISC then binds to and cleaves mRNA, knocking out the corresponding gene.

EXAMPLES

Example 1: Reactions in Small HD Apparatus

Two monomers were chosen as a model system—5'-adenosine monophosphate and 5'-uridine monophosphate—in their acid forms rather than as sodium salts. When dissolved in water at 10 mM concentration the pH of the solution is ~3. These two mononucleotides ordinarily form hydrogen-bonded base pairs in RNA. Polyadenylic acid (polyA) and polyuridylic acid (polyU) served as polynucleotide standards. These were mixed in 1:1 mole ratios with respect to the bases to produce double stranded RNA (polyAU).

Reaction Mixtures

A typical reaction mixture in the larger simulation chamber had 0.2 mL of 10 mM mononucleotides and 0.1 M monovalent salts (LiCl, NaCl, KCl, $NH_4Cl$). Variables that were tested included the initial pH, temperature, and ionic composition. Volumes were reduced to 0.1 mL when glass slides were used.

Isolation of Products

The polymer products were isolated in two ways: standard precipitation in ethanol, and purification with Invitrogen RNeasy spin tubes. Similar amounts were obtained, consistent with the presence of polymers that behaved like RNA. Depending on the conditions, typical yields ranged from 1% to 10% expressed as the fraction of the total weight of mononucleotide present.

Example 2: Analysis of Products

Products of the reaction were initially monitored by gel electrophoresis using Invitrogen 4% agarose gels with ethidium bromide staining. Some experiments used hand-poured 2% gels and the same intercalating dye. All of the gels are shown as inverted images to increase contrast. Products were also monitored by nanopore analysis, which has single molecule sensitivity. The nanopore method is described in Vercoutere et al. 2001, and De Guzman et al. 2006. Total yields were estimated by NanoDrop spectrophotometry. When the conditions were optimized for maximum yields, samples were analyzed by atomic force microscopy, high performance liquid chromatography (HPLC) and mass spectrometry.

The experiments described below were guided by predictions arising from the hypothesis that hydrothermal cycles can drive polymerization reactions and synthesis of double stranded products:

1. A standard dsRNA must be sufficiently stable to withstand multiple HD cycles at 85 C and pH 3.
2. If dsRNA is among the products, it should bind intercalating dyes like ethidium bromide during gel electrophoresis.
3. The polymers will exhibit hyperchromicity if duplex species are products.
4. Nanopore signals will resemble those expected for duplex species, rather than single stranded oligomers.
5. Atomic force microscopy should reveal short oligomers in the size range expected from gel analysis of products.
6. Electrospray and MALDI mass spectrometry of a known dsRNA should closely resemble that of the product.
7. If a template strand is present, the products should contain sequences complementary to the template sequences.
8. Amplification of template strands should be observable.

Stability of RNA

Figure 4A:
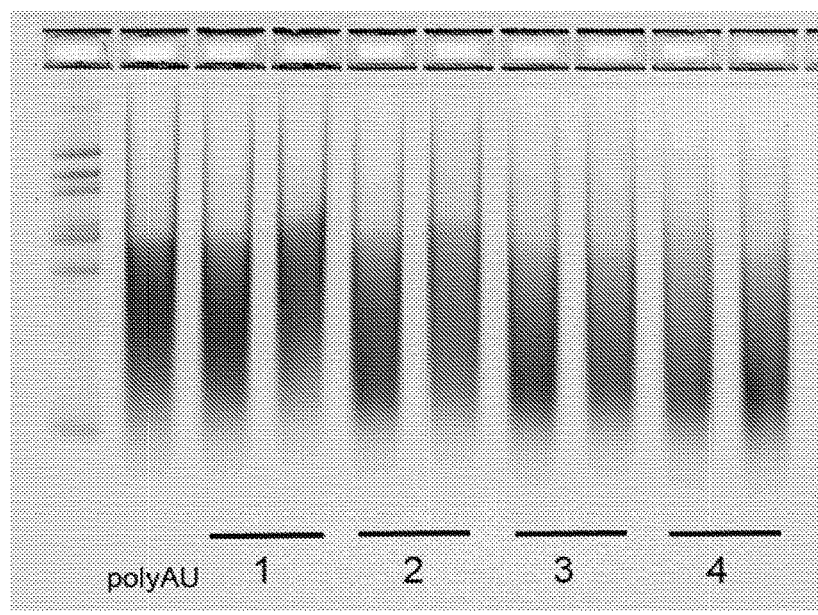
FIG. 4A, 4B, 4C is a photograph (4A) scan (4B) and graph (4C) showing hydrolysis of poly AU. The gels and scans are duplicate samples exposed to four HD cycles. The experiment began with 20 micrograms of polyAU, and the Y axis shows the micrograms of polymer remaining after each cycle.
Figure 4B:
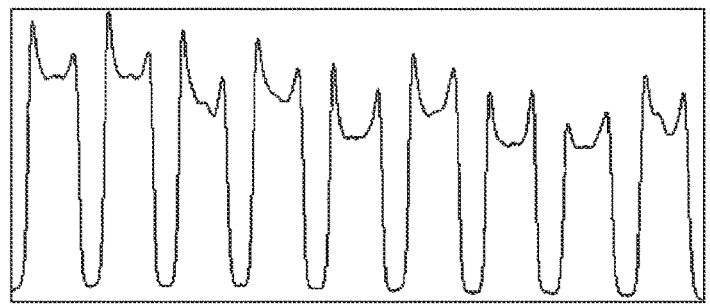
Figure 4C:
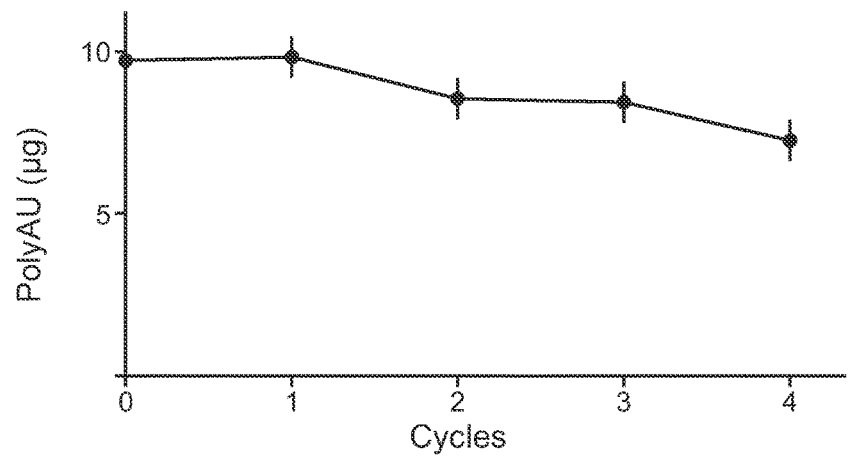

It was essential to establish the rate at which a known RNA sample undergoes hydrolysis during HD cycles at acid pH ranges and elevated temperatures. If RNA hydrolyzed completely in a single 2 hour cycle, there would be no reason to look for synthesis. It is generally considered that RNA is a fragile molecule, and most workers in the field would be surprised if extensive hydrolysis of the polyAU duplex standard did not occur. However, FIG. 4A shows a gel and NanoDrop™ UV-Vis analysis of polyAU duplex going through multiple HD cycles. Most of the polyAU survived four cycles. The gels and scans (4B) are duplicate samples exposed to four HD cycles. The experiment began with 20 micrograms of polyAU, and the Y axis shows the micrograms of polymer remaining after each cycle (4C). This shows that the hydrolysis of RNA polymers is not occurring during the HD cycles at a rate that will prevent polymerization by formation of the phosphate linkages.

Cycling Increases Yield of Polymers

Figure 5:
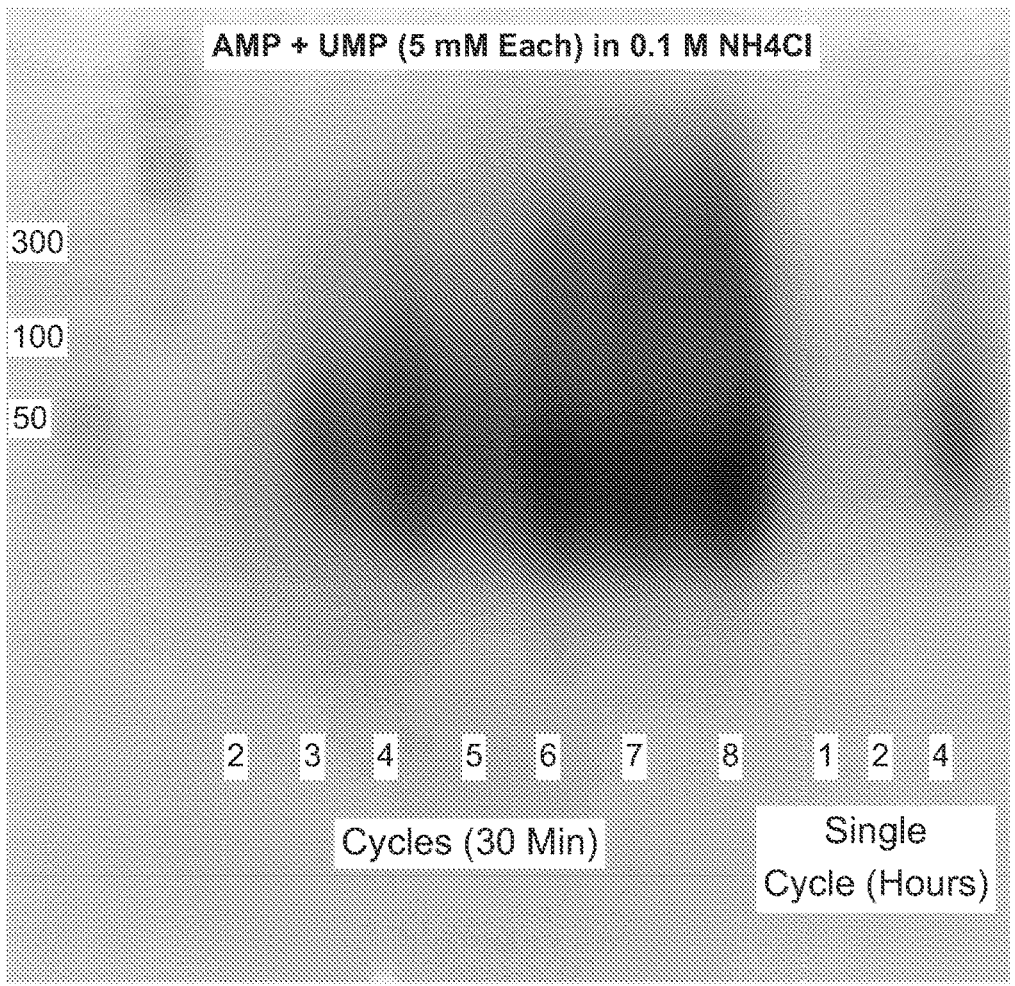
FIG. 5 is a photograph of a gel showing polymerization of AMP and UMP. It demonstrates the effect of cycles of HD on yield. A fluorescent dye (ethidium bromide) is used to stain the products of the reaction. The image is inverted so that the fluorescence is shown as dark against a light background.

FIG. 5 shows how the yield increases with the number of cycles, particularly the longer products in the 300mer range. Also note that a single cycle does not produce the same yield even though the total time (4 hours) is equivalent to 8 cycles of 30 minute duration.

Monovalent Ions Promote Yields of Polymers

Figure 6:
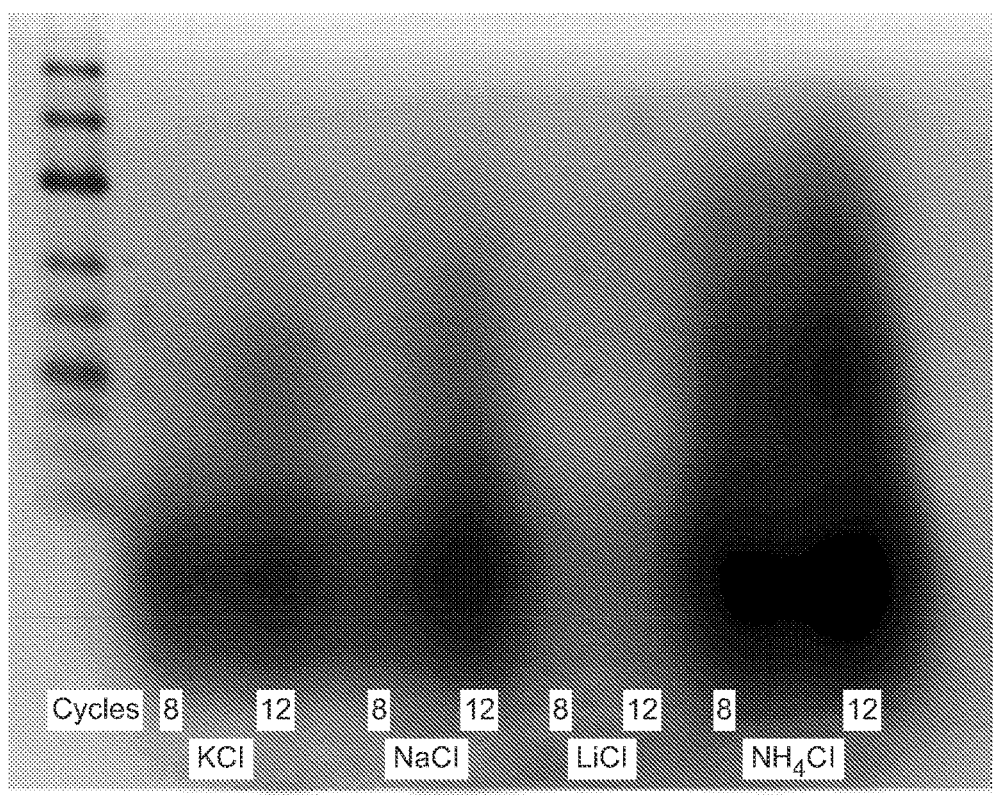
FIG. 6 is a photograph of a gel showing polymerization in the presence of different salts.

As noted earlier, if the HD cycles are run with monovalent salts present, yields of polymer are dramatically increased (FIG. 6). The salts are initially at 0.1 M concentration, and sodium, potassium and ammonium chloride all seem to catalyze polymerization, with $NH_4Cl$ having the greatest effect. Significantly, LiCl is ineffective. The lithium cation is strongly hydrated, which may explain why it is unable to catalyze a condensation reaction. The salt effects are summarized in Table 1.

FIG. 6 shows that polymer yields increased in the presence of monovalent salts. Ammonium chloride was most effective in promoting polymerization, while lithium chloride had virtually no effect. The hours are cumulative times of 30 minute HD cycles, so 4 hrs represent 8 cycles.

TABLE 1

Summary of salt effects on polymerization

| Salt | Polymerization |
|---|---|
| $NH_4 H_2PO_3$ | + |
| $NH_4CO_3$ | + |
| KCl | + |
| NaCl | ++ |
| $NH_4Cl$ | ++++ |
| LiCl | (no effect) |
| $NH_4$ molybdate | (no effect) |

Intercalation of Ethidium Bromide into dsRNA

Figure 7:
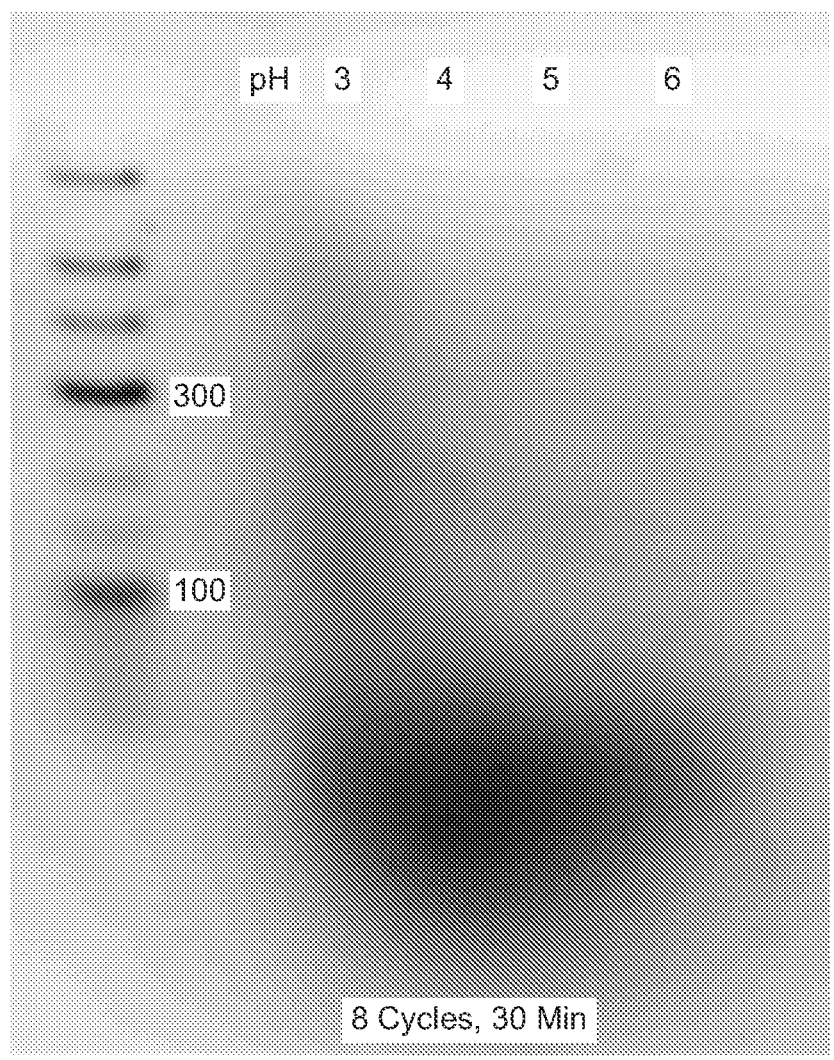
FIG. 7 is a photograph of a gel showing the effect of pH on the products of 4 HD cycles run with AMP and UMP as monomers. A low pH is required for the reaction to proceed.

It is well known that the fluorescence of certain dyes is markedly enhanced when they intercalate into double stranded polynucleotides. This effect is illustrated in FIG. 7, which shows a gel with polyA, polyU and the duplex species polyAU produced by mixing the two homopolymers in a 1:1 mole ratio of A:U. The homopolymers (2 μg) do not bind the dye, but simply mixing the polyA and polyU to produce the same amount of the duplex species polyAU gives a strongly fluorescent band due to ethidium intercalation. This result is significant, because the products of the HD polymerization reaction bind ethidium and are strongly fluorescent in the gels shown here.

Example 3: Acidic Conditions

Figure 8:
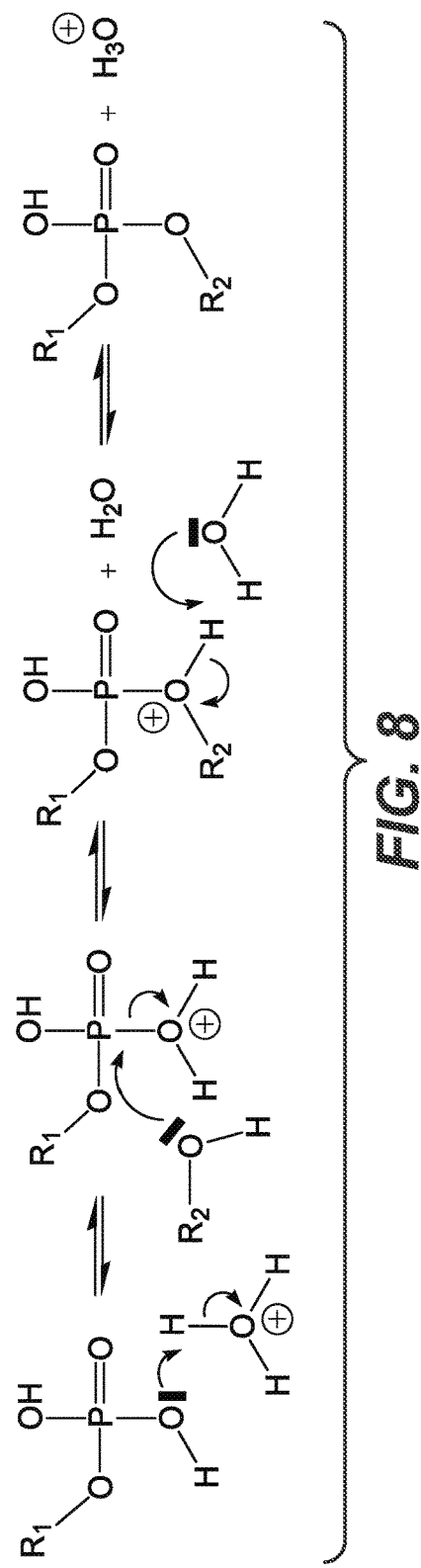
FIG. 8 is a diagram showing acid-catalyzed bond formation proposed as a polymerization mechanism in the present process.

An acidic pH is required to synthesize longer strands of polymer in the range of 100-300 nt, as shown in FIG. 7. FIG. 7 shows that a pH in the range of 3 produces more high MW product than processes carried out at higher pH. This is consistent with a mechanism involving acid catalyzed ester bond formation (FIG. 8). Although synthesis of the shorter oligomers (20-40mers) can occur over a broader pH range, there is virtually no product in alkaline conditions.

Example 4: Confirmation of RNA Polymerization—(RNase Digestion)

Figure 9:
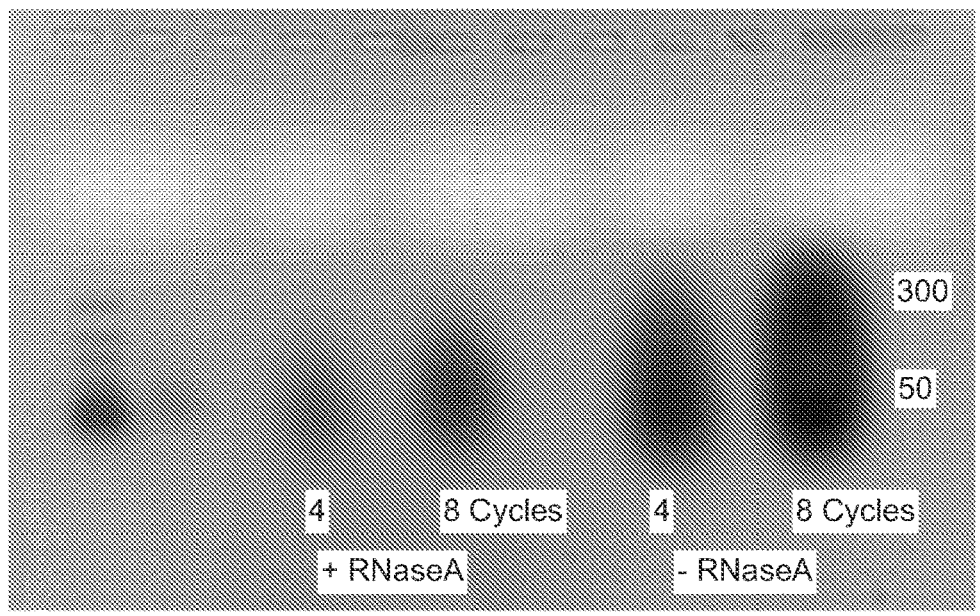
FIG. 9 is a photograph of a gel showing that RNase A cleaves the presently produced polymers, with longer strands more sensitive to the enzyme's action.

The polymers can be digested by RNase A, an enzyme that hydrolyzes the phosphodiester bonds formed by UMP (FIG. 9). This important result indicates that UMP has become incorporated in an RNA-like polymer that is recognized by an enzyme specific for RNA.

Example 5: Product Analysis

Hyperchromicity
UV spectra of samples were obtained while heating from room temperature to 90 degrees C. Most samples showed hyperchromicity that increased with temperature, then decreased upon cooling. This is consistent with the presence of double stranded products.

Nanopore Analysis of Products
The majority of blockades seen in a nanopore instrument were in the range of several milliseconds duration and approximately 25% amplitude (data not shown). This duration and amplitude is consistent with the presence of dsRNA, because single strand duration would be measured in tens of microseconds with blockade amplitudes ranging from 80-90%.

Figure 10:
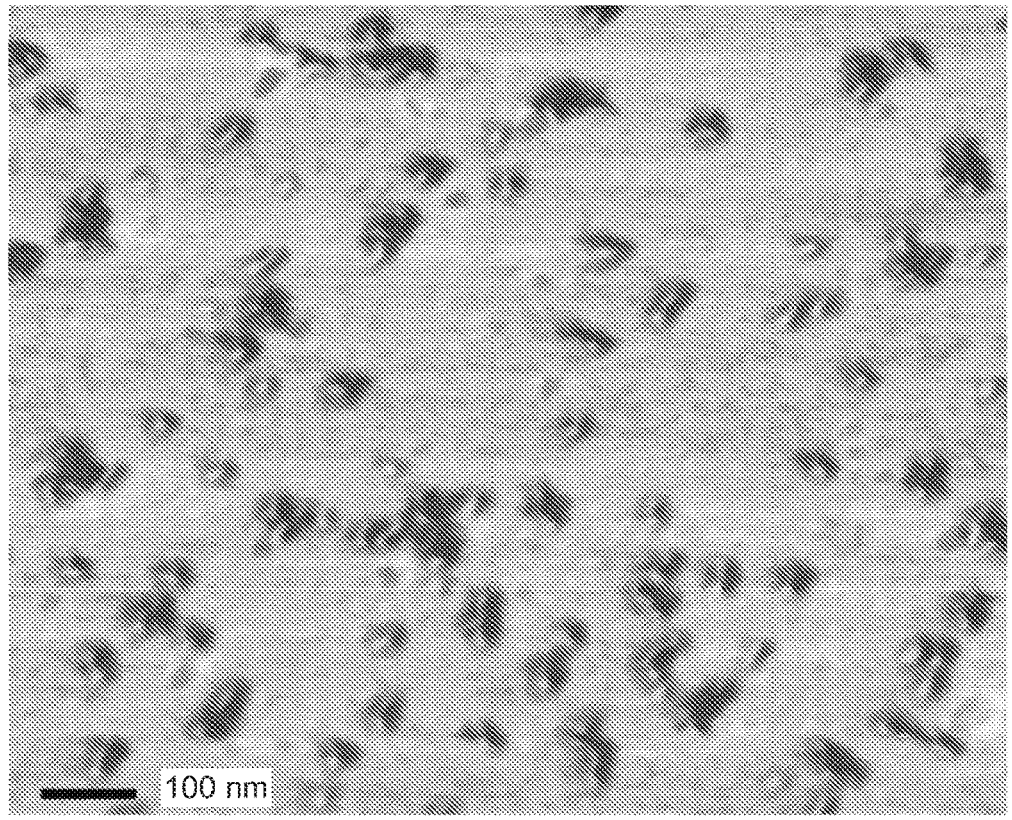
FIG. 10 is an image from atomic force microscopy showing evidence of duplex RNA.

Atomic Force Microscopy
A solution of products was dried on freshly cleaved mica sheet, then rinsed in deionized water and dried again. Images of samples showed what would be expected of duplex species in the size range of 50-100 nt, which was shown (FIG. 10).

Products were also analyzed by mass spectrometry. A DNAPac PA100 column designed to separate oligonucleotides was used in conjunction with the electrospray mass spectrometer facility at UC Santa Cruz. Mass spectra of the standard polyAU duplex and the putative dsRNA product demonstrated a polymeric structure of the synthesized polynucleic acids (data not shown). The patterns are similar, consistent with the presence of dsRNA among the products.

Example 6: "Feeding" Experiment (Template Directed Synthesis)

It is possible that dsRNA species were not only synthesized, but in fact could act as templates during multiple cycles, analogous to the amplification of dsDNA in the polymerase chain reaction. To test this idea, we performed a feeding experiment in which fresh substrates (nucleic acid monomers) were added after 8 or 12 HD cycles of 30 minutes, followed by another 8 or 12 cycles. If no templating occurred, the amount of products would double after feeding, but if the existing polymer strands were serving as templates more than a simple doubling would be observed. In other words, initial templates form new polynucleotides that also serve as templates for additional mononucleotides, creating an exponential increase in polynucleotides.

Figure 11A:
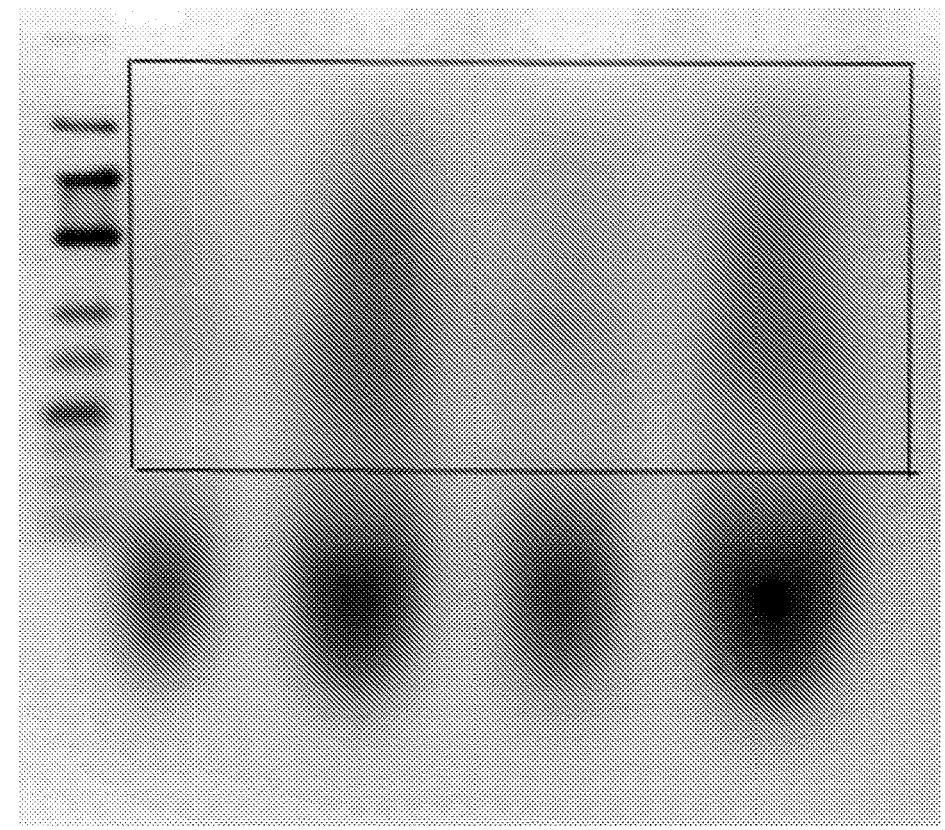
FIG. 11A, 11B shows a gel (11A) and scan (11B) of longer polymers (indicated by box in 11A) showing the products of a feeding experiment.
Figure 11B:
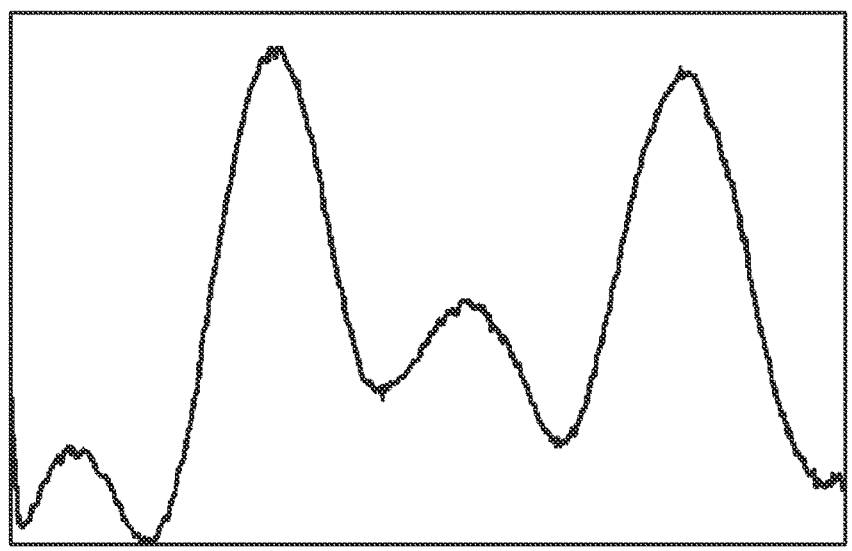

FIG. 11A shows a gel and a densitometer scan of higher RNA polymers obtained as a result of the feeding of additional AMP and UMP during the process. The two lanes on the left are 8 cycles and the two lanes on the right at 12 cycles before and after adding AMP and UMP. A scan of the gel in the lower panel clearly indicates that more than twice the amount of long chain product has been synthesized.

Template directed synthesis can be carried out by adding a desired template and the required mononucleotides. Using the present description as a guide, one may use a DNA or RNA strand with the desired sequence, put it through multiple HD cycles with mononucleotides present, then isolate and purify the products. This should work very well to synthesize siRNA, which is a dsRNA with 20 or so base pairs. Further details on sequences and uses of such molecules may be found, e.g., in Christian et al. "Short interfering nucleic acid hybrids and methods thereof," US 20040053289, published Mar. 18, 2004.

FIG. 12 illustrates the different possible structures of random RNA polymers produced by the present process.

Addition of a template of a desired sequence is carried out by providing a warm temperature, (e.g. 70-90 deg. C.) and the salts, acid, and monomers described above. In addition a template polynucleotide, that is DNA or RNA is added. For example, equal amounts of dTMP, dGMP, dCMP and dAMP at a total nucleotide concentration of 10 mg/ml are mixed in 0.5 ml total of MilliQ $H_2O$+salt. Template oligomer (5 mg) is added and the mixture is incubated at 90 deg. C. for 2 h under a continuous gentle stream of $CO_2$ gas. The $CO_2$ serves to remove water. After rehydrating the reaction mixture for 10 min with 0.5 ml of salt solution, the incubation is repeated. The incubation and rehydration cycle is repeated 5 times and 0.5 ml MilliQ $H_2O$ is used for the last rehydration. The synthesized DNA may be purified from the solution and further amplified by PCR.

Example 7: Increasing Polymer Yield Synthesis—Based on Manuscript

As previously, two monomers were chosen adenosine 5'-monophosphate (AMP) and uridine 5'-monophosphate (UMP) in their acid forms rather than as sodium salts (Sigma-Aldrich). When dissolved in water at 10 mM concentration the pH of the solution is ~2.5. Commercial polyadenylic acid (polyA) and polyuridylic acid (polyU) were used as polynucleotide control standards (Sigma-Aldrich). These were mixed in 1:1 mole ratios with respect to the bases to produce double stranded RNA (polyA-polyU). The effects on oligomerization of a variety of monovalent salts, including LiCl, NaCl, KCl, and $NH_4Cl$ were tested. During evaporation, the salts formed crystalline films when their solubility was exceeded. The growing crystals excluded other solutes such as the mononucleotides, producing highly concentrated eutectic phases within the salt matrix.

A Laboratory Simulation of HD Cycles
Simulations were carried out using glass slides with two wells on each slide that hold 0.1 mL of the reaction mixture.

Four slides were arranged on a laboratory hot plate set at the desired temperature range, and a plastic flow box with 8 small holes (1 mm diameter) was set on the slides. Each hole was placed directly over a well so that carbon dioxide gas flowed onto the mixture at approximately 1 cc/sec into each well. The gas was used to exclude oxygen, but also to carry away water vapor from condensation reaction as ester bonds formed, thereby preventing hydrolytic back reactions.

Reaction Mixtures

Mononucleotides, AMP (10 mM) and UMP (10 mM), were initially mixed in a 1:1 volume ratio. The mononucleotides solution and 0.1 M monovalent salts were mixed in a 2:1 volume ratio so that the initial concentrations were 3.3 mM AMP and UMP, together with 0.033 M salt. Because water evaporated during dehydration, these dilute solutions become highly concentrated and finally dry, so it is the ratios that are significant rather than the initial concentrations. In a typical experiment, the reactants were exposed to 1-16 cycles of wetting and drying. The temperature (85° C.) and flow of carbon dioxide caused drying within 1-2 minutes. After each dehydration phase of 30 minutes, the samples were dispersed in 0.1 mL of 1.0 mM HCl to maintain acidity, followed by the next dehydration cycle. Variable experimental parameters included initial pH, temperature, the time given to each cycle and the numbers of cycles. At the end of the cycle series, the samples were dissolved in 0.1 mL of water.

Isolation of Products

The polymer products were isolated by standard precipitation in ethanol (2.5× volume ethanol 100%, 1/10 volume sodium acetate 3 M pH 5.2, 1.6 µL linear acrylamide 5 mg/mL (Fischer scientific) for 700 µL of reaction mixtures, followed by incubation at −20° C. overnight). The pellets were consistent with polymers that behaved like RNA. Quantitative analysis was performed by UV absorbance with a NanoVue instrument calibrated for RNA to estimate yields of products. Depending on the conditions, typical yields ranged from 1% to 40% expressed as the fraction of the total weight of mononucleotides present, and over 55% if additional monomers were added during cycling.

Characterization of Products

As described above, double-stranded polynucleotide structure was shown by ethidium bromide, alkaline hydrolysis, RNase hydrolysation, hypochromicity, nanopore analysis and microscopy.

Effect of Monovalent Cations on Polymerization

When the HD cycles were run with monovalent salts in the reaction mixture, yields of polymer were dramatically increased compared to absence of salts. Furthermore, the products were stained by ethidium bromide, an intercalating dye, suggesting that base stacking was present. Sodium, potassium and ammonium chloride all promoted synthesis of polymers containing AMP and UMP as monomers. Products ranging from 10 to 300 nucleotides with a peak around 100 mers were detected. $NH_4Cl$ had the greatest effect, but products from LiCl produced only a weak band in the gel even though the yield measured by ethanol precipitation was in the same range as $NH_4Cl$ (Table 2). The $A_{260}/A_{280}$ ratio provides an estimate of how much of the absorbance is due to polymers and how much to monomers. A ratio of 2 corresponds to RNA while a ratio of 3.4 is observed for monomers. The high ratio with LiCl indicates that the product has relatively short strands of oligomer lacking base stacking compared with the other salts.

Mixtures of AMP 10 mM+UMP 10 mM+monovalent salt 0.1 M (LiCl, KCl, NaCl and NH4Cl) in 1:1:1 volume ratio were submitted to 16 HD cycles of 30 minutes. Table 2 below shows yields of polymers synthesized and ratio A260/A280 measured by UV absorbance with a NanoVue instrument. Yields are values from duplicate samples, and were calculated as the percent by weight of the original AMP and UMP present in the mixture

TABLE 2

Effect of monovalent salts on polymerization.

| Salt | Yield (%) | $A_{260}/A_{280}$ |
| --- | --- | --- |
| LiCl | 38; 42 | 3.4 |
| NaCl | 16; 18 | 2.1 |
| KCl | 25; 29 | 2.0 |
| $NH_4Cl$ | 34; 37 | 2.0 |

Yields were highest with LiCl, $NH_4Cl$, KCl and NaCl, in that order, but the LiCl product was less stained by ethidium, probably because the oligomers were shorter with decreased base stacking.

Cycling Increases Yield of Polymers

The optimum conditions for the polymerization process were determined by performing a set of experiments using a variety of controls and conditions including the number of cycles, duration of the cycles, pH and temperature. The synthesis of polymers is the most efficient at high temperature (around 85° C.), at acidic pH (3) and in the presence of $CO_2$ stream. Without wishing to be bound by any theory, the above suggests that synthesis of the ester bond is an acid catalyzed mechanism and that $CO_2$ plays an essential role in the polymerization process. Most of the product appeared to be polymers from 10 to 300 nucleotides long. Finally, the dehydration phase appeared to be essential for the polymerization process since a minimum of 30 minutes of drying at each cycle is necessary to synthesize the 300 nt species (data not shown).

Multiple HD cycles, 30 minutes each, were found to be more effective than a long single cycle. It is significant that longer products accumulate in later cycles, suggesting that ligation of shorter chains may be occurring.

Role of $NH_4^+$ Cations in Promoting Polymerization

Figure 14:
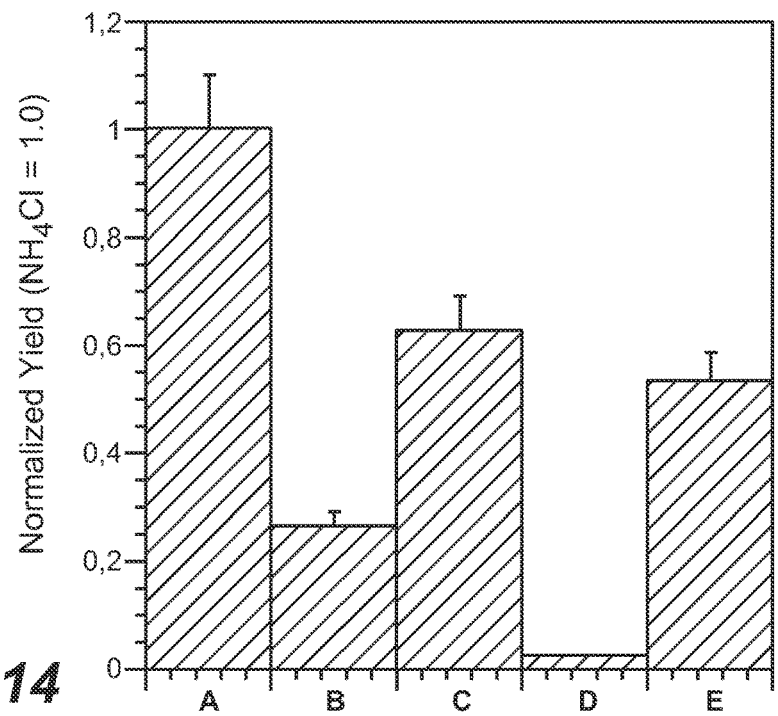
FIG. 14 is a histogram showing yields obtained from different salts. Lane A: NH$_4$Cl; lane B: C$_{19}$H$_{42}$BrN; lane C: HCO$_2$NH$_4$; lane D: (NH$_4$)$_6$Mo$_7$O$_{24}$4H$_2$O; lane E: NH$_4$H$_2$PO$_4$.

Because $NH_4Cl$ seemed to have the greatest effect on yields of polymers, a series of further experiments were conducted. FIG. 3 shows results with different ammonium salts, including ammonium phosphate, ammonium molybdate, and ammonium formate. Only the ammonium formate yielded polymers ranging from 10 to 300 nucleotides in length but in lesser amounts compared to ammonium chloride. The importance of the chemical effect of the ammonium cation in this polymerization process was also tested by substituting tetramethylammonium chloride for ammonium chloride. FIG. 14 shows polymer synthesis after 8 hours of 30 minutes HD cycles. Yields are normalized for comparison, taking the products in the presence of $NH_4Cl$ as 1.0. Salts, lane A: $NH_4Cl$; lane B: $C_{19}H_{42}BrN$; lane C: $HCO_2NH_4$; lane D: $(NH_4)6Mo_7O_{24}4H_2O$; lane E: $NH_4H_2PO_4$. FIG. 14 shows that tetramethylammonium chloride also produced polymers ranging from 10 to 300 nucleotides in length but with lower efficiency than ammonium chloride.

This suggests that $NH_4^+$ might have chemical effects induced by its protons coupled to the ordering effects on the mononucleotides.

Kinetics of Oligomerization

The oligomerization process in the presence of ammonium chloride follows an exponential curve, and reaches a plateau after 30 hours of wet-dry cycles with a yield of 40%

Figure 15:
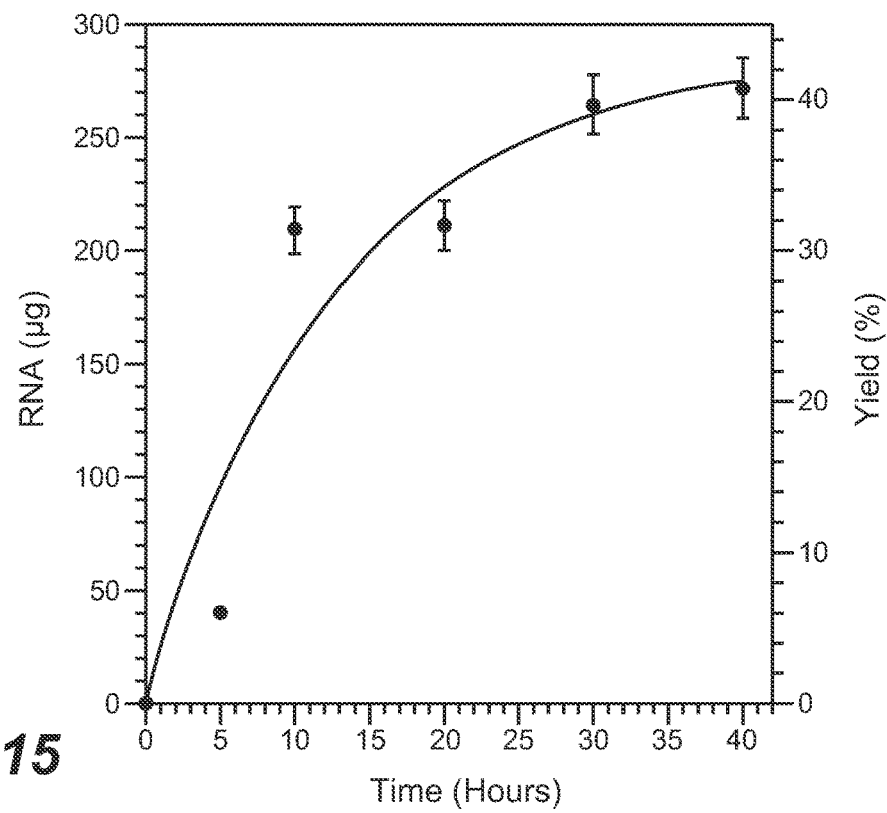
FIG. 15 is a line graph RNA kinetics of oligomerization experiments. Mixture of AMP 10 mM+UMP 10 mM+NH4Cl 0.1 M (1:1:1 volume ratio) showing the total amount and yield of products over multiple cycles. Each hour has two 30 minutes cycles, so 40 hours represents 80 cycles.

(FIG. 15). FIG. 15 shows results from Mixture of AMP 10 mM+UMP 10 mM+NH$_4$Cl 0.1 M (1:1:1 volume ratio) showing the total amount and yield of products over multiple cycles. Each hour has two 30 minutes cycles, so 40 hours represents 80 cycles.

Control of Nucleotide Concentration: Nucleotide Feeding

To determine whether the plateau was due to exhaustion of monomers, a feeding experiment was performed in which fresh monomers were added every 2 hours (4 cycles). An enhancement of oligomerization occurred when cycling is accompanied by regular additions of monomers. A yield of 58% is obtained after 5 feeding steps (final concentration of nucleotides equal to 60 mM) whereas for the same concentration (60 mM) present at the beginning of the experiment, the yield is 37%. This means that controlling nucleotides concentration by stepwise additions enhances the polymerization process in comparison to nucleotide pool at an equivalent concentration.

The plateau can be due to an equilibrium between synthesis and hydrolysis, although degradation of nucleotides over time may also contribute. FIG. 6 shows that longer products accumulate in later cycles. Indeed, there is an enhancement of the production of short fragments (10 and 150 nts) after few cycles, and then their presence decreases as a function of time whereas the long polymers (700 and 1000 nts) accumulate in the later cycles. Lengthening may occur either by elongation and/or by ligation of short fragments.

Example 8: Preparation of a Short Interfering RNA (siRNA)

Hydration/Dehydration Cycles

Processing of reactants was carried out in two ways. The first was in the robotic cycling apparatus described above. A simpler alternative for smaller numbers of samples was carried out using glass slides with two wells on each slide that hold 0.1 mL of the reaction mixture. Four slides were arranged on a laboratory hot plate set at the desired temperature range, and a plastic flow box with 8 small holes (1 mm diameter) was set on the slides. Each hole was placed directly over a well so that carbon dioxide gas flowed onto the mixture at approximately 1 cc/sec into each well. The gas was used to exclude oxygen, but also to carry away water vapor from condensation reaction as ester bonds formed, thereby preventing hydrolytic back reactions.

Reaction Mixtures

Mononucleotides, AMP (10 mM) and UMP (10 mM), were either used singly or as a mixture (1:1 volume ratio). The mononucleotide solution and 0.1 M monovalent salts were mixed in a 2:1 volume ratio so that the initial concentrations were 3.3 mM AMP and UMP, together with 0.033 M salt. Because water evaporated during dehydration, these dilute solutions become highly concentrated and finally dry, so it is the ratios that are significant rather than the initial concentrations. In a typical experiment, the reactants were exposed to 1-16 cycles of wetting and drying. The temperature (85° C.) and flow of carbon dioxide caused drying within 1-2 minutes. After each dehydration phase of 30 minutes, the samples were dispersed in 0.1 mL of 1.0 mM HCl to maintain acidity, followed by the next dehydration cycle. At the end of the cycle series, the samples were dissolved in 0.1 mL of water and yields were determined with a Nanodrop instrument. Composition was monitored by gel electrophoresis using ethidium bromide as a marker for double stranded products, and the presence of single stranded products was confirmed by nanopore analysis.

Introduction of Templates

When it was desired to introduce templates, the nucleic acid template are added to the reaction mixture and processed as described above. In one example, 20 micrograms of polyuridylic acid was added together with dAMP. Approximately 30 micrograms of product was recovered by ethanol precipitation after 4 cycles. An aliquot of the product was analyzed by gel electrophoresis using ethidium bromide as an intercalating dye, and a long fluorescent streak appeared, indicating that the dye had stained a double stranded product. The streak began at the 20mer range as indicated by a DNA ladder, and extended nearly to the top of the gel. This would be expected because polyU is a mixture of shorter and longer homopolymers.

siRNA

Either a known siRNA can be used, or a siRNA can be designed using available software. See, e.g. US 20140161894, "Sirna silencing of genes expressed in cancer," US 20050058982, "Modified small interfering RNA molecules and methods of use," U.S. Pat. No. 8,318,689, "SiRNA-based cancer treatment," U.S. Pat. No. 7,947,659, "iRNA agents targeting VEGF," etc.

The template is a polynucleotide that is DNA and encodes both strands of the desired siRNA. It may further comprise intervening sequences between the two RNA sequences being formed on the template. The template may include restriction enzyme sited between the two strands being formed, to facilitate assembly of the two complementary strands of the siRNA. The template then will be about 50-100 in length and will be single-stranded.

The necessary RNA monomers are incubated with a number of template molecules in the acidic/heat/salt combination described above.

The following siRNA construct is prepared for study. It inhibits expression of the luc gene. Sequence of the luc gene (may be found, for example, at GenBank: KJ081213.1. The firefly luciferase gene is further described at Wetr et al., "Firefly Luciferase Gene: Structure and Expression in Mammalian Cells," Mol. Cell. Biol., 7(2):725-737 (1987). As described there, luciferase expression is a means of monitoring expression of a gene. It may be used here to measure the uptake and effectiveness of a SiRNA product. The siRNA prepared has the following sequences:

```
                                           (SEQ ID NO: 1)
               5'-ACGCCAAAAACAUAAAGAAAG-3'

(SEQ ID NO: 2)
               3'-UCUGCGGUUUUUGUAUUUCUU-5'
```

To produce this above duplex RNA, one may synthesize a single single-stranded DNA template (e.g SEQ ID NO: 3) or a pair of ssDNA templates. The templates incorporate sequences for the two complementary base sequences, e.g. SEQ ID NO: 1 and SEQ ID NO: 2 above. If a single template is used for both RNAs, an abasic nucleotide may be used to separate the sequences encoding the two siRNA strands. Restriction sites may also be engineered into a single template.

Further constructs may be designed as described at https (colon slash slash) www (dot) broadinstitute.org/rnai/public/gene/details?geneId=TRCG0000060314.

The DNA template is cycled multiple times under the above-described conditions of salt, acidity, heat, atmosphere, etc., with all four ribonucleotide monophosphates present, and each cycle synthesizes the desired complementary RNA 21mers that will assemble into duplex strands.

Significantly, the DNA template can be covalently attached to silica beads so that product RNA can simply be washed off after each cycle. Errors are likely to occur as the mononucleotides are polymerized on the template, but the RNA strands with the correct sequence will form stable duplex species that can be easily purified, for instance by electrophoresis.

Other RNA Products

The present examples also can be applied to other RNA therapeutic molecules, using the template-driven in vitro synthesis described here. RNA products can be, for example, RNA aptamers, e.g. as described in Wang et al., "Aptamers as therapeutics in cardiovascular diseases," Curr Med Chem. 2011; 18(27):4169-74. Also contemplated are RNA antisense, e.g. as described in Weiss et al, "Antisense RNA gene therapy for studying and modulating biological processes" Cell. Mol. Life Sci., 55:334-358, 1999. Also, microRNAs are made by Dicer, but microRNA derive from single-stranded RNAs that fold back on themselves to generate small regions of double-stranded RNA—so called "stem-loops"— instead of the long double-stranded RNA that produces siRNAs. Most anti-miRs use modifications of the typical nucleic acid ribose sugar backbone with 2' modifications. Such modified nucleotides can be incorporated using the present, non-enzymatic methods. (See, Montgomery et al., "Therapeutic inhibition of mir-208a improves cardiac function and survival during heart failure," Circulation. 2011; 124:1537-1547.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. An in vitro method for preparing a ribonucleic acid (RNA) from a plurality of mononucleotides, comprising:
   (a) providing an acidic solution free of polymerase and lipids, but containing a monovalent salt and mononucleotides selected from the group consisting of adenosine 5'-monophosphate, uridine 5'-monophosphate, guanosine 5'-monophosphate, and cytidine-5'-monophosphate;
   (b) drying the acidic solution of step (a);
   (c) resolubilizing the solid generated in step (b); and (d) repeating the drying and resolubilizing steps (b) and (c) a plurality of times causing a reaction linking the mononucleotides thereby synthesizing the RNA, wherein the monovalent salt is a metal halide salt or an ammonium halide salt.

2. The method of claim 1, wherein the monovalent salt is present in the acidic solution at a present concentration of at least 0.01 M.

3. The method of claim 1, further comprising wherein the drying comprises heating the acidic solution of step (a).

4. The method of claim 3, wherein the heating the acidic solution comprises heating the acidic solution to a temperature between 80° C. and 90° C.

5. The method of claim 1, wherein the acidic solution is adjusted to a pH between 2 and 4.

6. The method of claim 1, wherein the monovalent salt concentration is between 0.05 and 2M in solution.

7. The method of claim 3, wherein the mononucleotides are present in the solution at a concentration of at least 1 millimolar.

8. The method of claim 1, wherein the method further comprises recovering the RNA.

9. The method of claim 8, wherein recovering the RNA comprises isolating the RNA via ethanol precipitation.

10. The method of claim 1, wherein the monovalent salt is a metal halide salt.

11. The method of claim 10, wherein the metal halide salt is selected from the group consisting of NaF, CsCl, NaBr, $NaClO_4$, NaCl, and KCl.

12. The method of claim 11, wherein the metal halide salt is present in the acidic solution at a concentration between 0.05 M and 2M.

13. The method of claim 1, wherein the monovalent salt is an ammonium halide salt.

14. The method of claim 13, wherein the ammonium halide salt is $NH_4Cl$.

15. The method of claim 14, wherein the $NH_4Cl$ is present in the acidic solution at a concentration between 0.05 M and 2M.

16. The method of claim 1, wherein the RNA has a length of at least 10 bases.

17. The method of claim 1, further comprising wherein the reaction is carried out under anaerobic conditions.

18. The method of claim 17, wherein the anaerobic conditions are formed by adding a $CO_2$ atmosphere to the reaction.

19. An in vitro method for preparing a ribonucleic acid (RNA) of a desired sequence, comprising:
(a) providing an aqueous solution adjusted to be between pH 2 and 4, free of polymerase and lipids, and comprising:
mononucleotides selected from the group consisting of adenosine 5'-monophosphate, uridine 5'-monophosphate, guanosine 5'-monophosphate, and cytidine-5'-monophosphate, each at a concentration of from 0.001M to 3M;
a monovalent salt selected from the group consisting of NaF, CsCl, NaBr, $NaClO_4$, NaCl, KCl, and $NH_4Cl$ at a concentration of at least 0.1 M; and
a template polynucleotide complementary to the desired sequence;
(b) drying the aqueous solution of step (a);
(c) resolubilizing a solid generated in step (b); and
(d) repeating the drying and resolubilizing steps (b) and (c) a plurality of times causing a reaction linking the mononucleotides thereby synthesizing the RNA,
wherein steps (b)-(d) are carried out in an anaerobic environment.

20. An in vitro method for synthesizing a ribonucleic acid (RNA) from a plurality of mononucleotides, comprising:
(a) providing an acidic solution free of polymerase and lipids, but containing mononucleotides selected from the group consisting of adenosine 5'-monophosphate, uridine 5'-monophosphate, guanosine 5'-monophosphate, and cytidine-5'-monophosphate and a monovalent salt selected from the group consisting of NaF, CsCl, NaBr, $NaClO_4$, NaCl, KCl, and $NH_4Cl$ and said monovalent salt being at a concentration between 0.05 M and 2M;
(b) drying a solution of step (a) by heating the solution to a temperature between 80° C. and 90° C.;
(c) resolubilizing the solid generated in step (b); and
(d) repeating the drying and resolubilizing steps (b) and (c) a plurality of times to generate the RNA.

* * * * *